(12) United States Patent
Duckett et al.

(10) Patent No.: US 6,434,847 B1
(45) Date of Patent: Aug. 20, 2002

(54) METHODS AND APPARATUS FOR DETERMINING THE LOCATION OF A SHAFT WITHIN A VESSEL

(75) Inventors: Gregory S. Duckett, Raleigh; C. J. Anthony Fernando, Durham; Michael F. Haw, Raleigh, all of NC (US)

(73) Assignee: Varian, Inc., Palo Alto, CA (US)

( * ) Notice: Subject to any disclaimer, the term of this patent is extended or adjusted under 35 U.S.C. 154(b) by 0 days.

(21) Appl. No.: 09/432,704

(22) Filed: Nov. 2, 1999

(51) Int. Cl.⁷ .................... G01B 11/00; G01B 11/14; G01B 7/14; G01B 7/312; G01M 19/00
(52) U.S. Cl. .................... 33/520; 73/1.81; 73/1.79; 73/865.9; 73/866; 702/87; 702/150; 702/158; 702/94; 702/97; 702/166; 356/615
(58) Field of Search .................. 33/520, 533; 73/865.9, 73/1.81, 1.79, 1.01, 1.88, 866; 702/150, 158, 87, 166, 94, 97; 356/615, 617, 625; 250/231.18, 252.1 A

(56) References Cited

U.S. PATENT DOCUMENTS

| 4,141,243 A | * | 2/1979 | Van Tessel et al. ........ 73/119 A |
| 4,711,034 A | * | 12/1987 | Koitumi ................ 33/832 |
| 4,769,538 A | * | 9/1988 | Krieger et al. .......... 116/202 X |
| 5,403,090 A | | 4/1995 | Hofer et al. |
| 5,589,649 A | | 12/1996 | Brinker et al. |
| 5,639,953 A | | 6/1997 | Renslow |
| 5,827,984 A | * | 10/1998 | Sinnreich et al. .............. 73/866 |
| 5,979,069 A | | 11/1999 | Hayashida et al. ........... 33/556 |
| 5,983,515 A | | 11/1999 | Brinker et al. |

FOREIGN PATENT DOCUMENTS

| EP | 833 132 A2 | * | 4/1998 | ........... G01D/11/24 |
| WO | 98/05957 | * | 2/1998 | .......... G01N/33/15 |

* cited by examiner

Primary Examiner—Thomas P. Noland
(74) Attorney, Agent, or Firm—Jenkins & Wilson, P.A

(57) ABSTRACT

Apparatus and methods for measuring the amount by which the centerline of a shaft disposed in a vessel is offset from the central vertical axis of the vessel, and for measuring the height of such shaft above the inside bottom of the vessel. Apparatus includes a shaft centerline offset measurement device, a shaft height measurement device, and a control/display console. Each measurement device includes a transducer or optical encoder for sensing a displaced position of a biased plunger to which a code strip is mounted. The devices may be combined into a single shaft offset and height measurement device. Improved methods include calculating shaft offset based on a plurality of readings from the transducer, and applying trigonometric relationships. The apparatus and methods are particularly useful in the verification of paddle or basket shafts utilized in dissolution testing stations, so that the dissolution testing protocol complies with government agency guidelines.

31 Claims, 17 Drawing Sheets

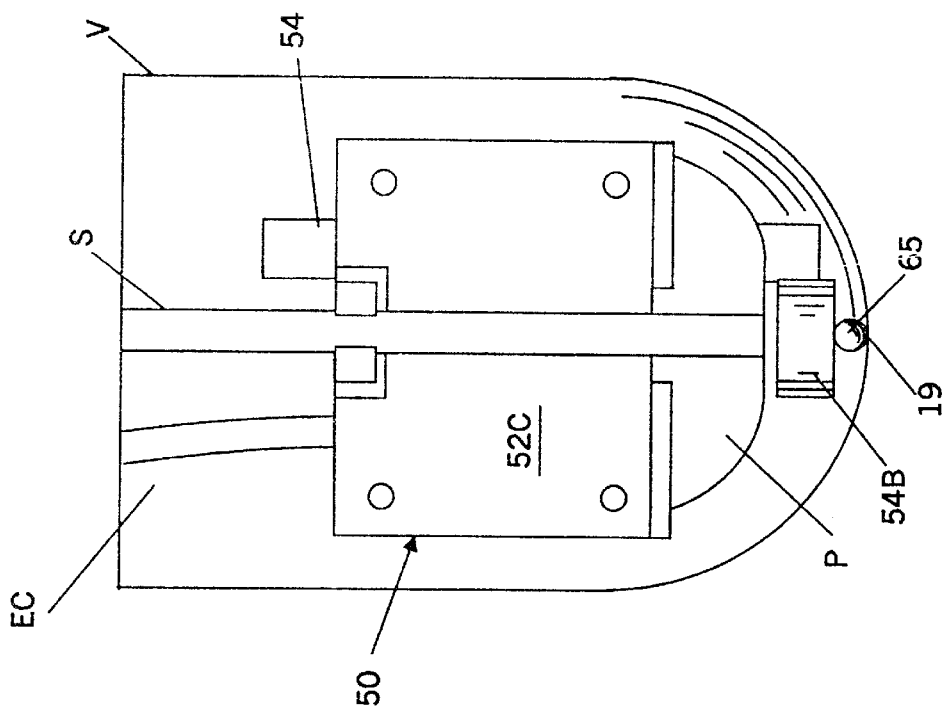
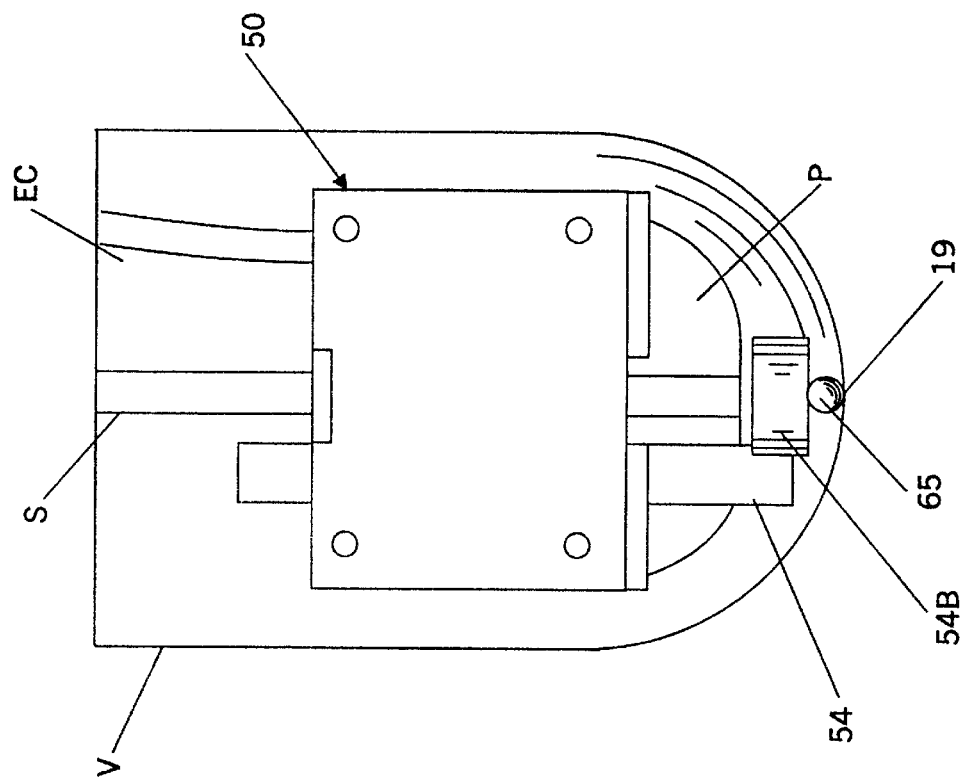

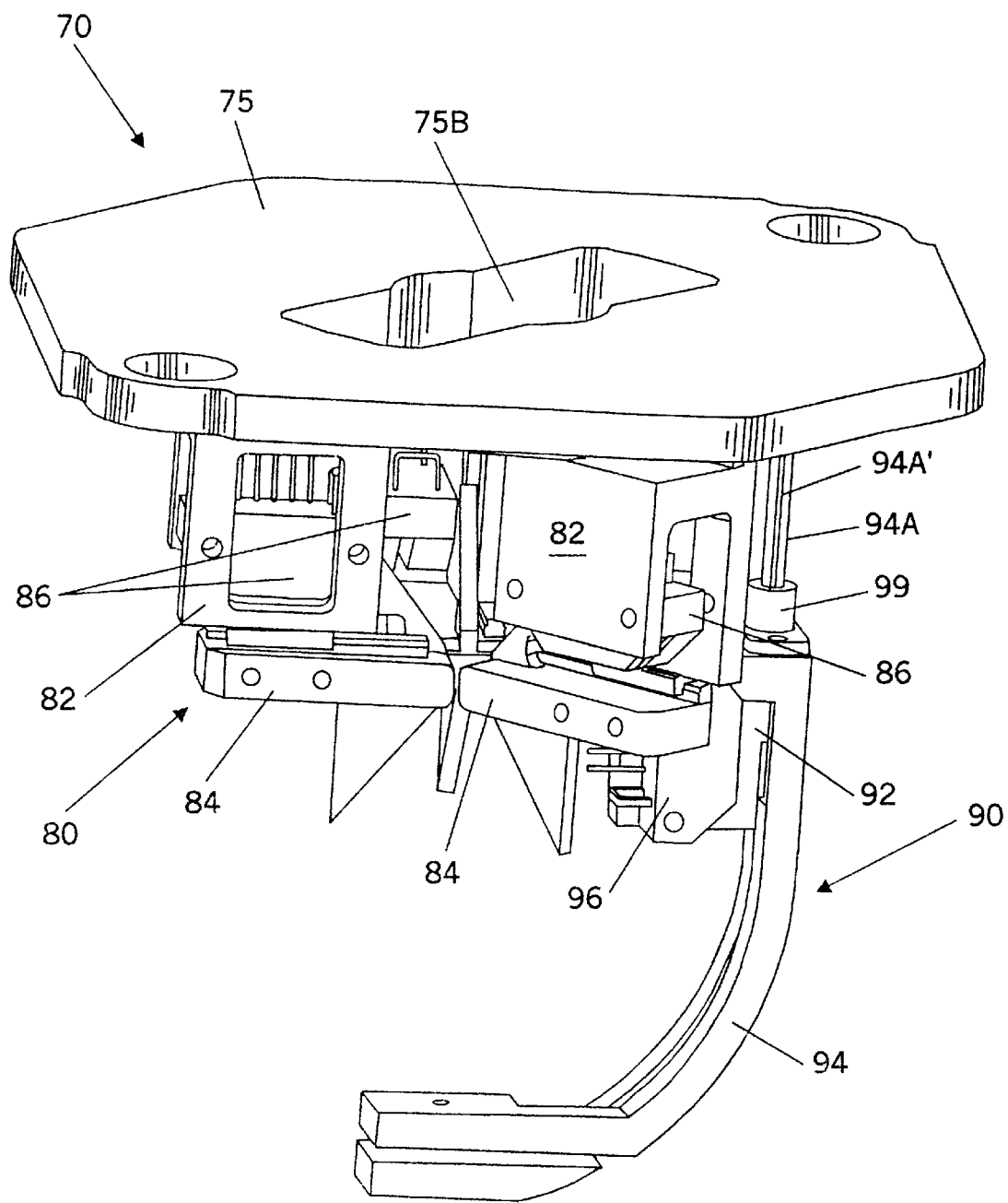

| FIG. 13A |
| FIG. 13B |

METHODS AND APPARATUS FOR DETERMINING THE LOCATION OF A SHAFT WITHIN A VESSEL

TECHNICAL FIELD

The present invention generally relates to measurement of the distance of a shaft from the bottom of a vessel and the amount by which the shaft is offset from the center of the vessel. More particularly, the present invention relates to the precise measurement of shaft height and shaft offset in vessels employed in dissolution testing systems.

BACKGROUND ART

In the pharmaceutical industry, dissolution testing and analysis is required to be performed on samples taken from batches of tablets or capsules manufactured by pharmaceutical companies in order to assess efficacy and other properties. Dissolution analysis by automated means has become popular for increasing throughput and improving accuracy, precision, reliability, and reproducibility. Automation also relieves the tedium of manually performing a variety of requisite procedures, including: handling and delivering dosage units such as capsules and tablets; monitoring dissolution system parameters; manipulating the shafts carrying the agitation paddles or sample baskets; recording, displaying and printing accumulated data and test results; and cleaning and filtering the vessels employed in such procedures.

Despite the benefits accruing from automation, validation of the procedures employed in dissolution testing and analysis remains a critical consideration. A typical dissolution test requires, among other things, that a rotatable shaft equipped with a paddle or basket be properly positioned in the center of, and properly located a specified distance from the bottom of, a dissolution test vessel prior to conducting the test. The USP has promulgated guidelines for the pharmaceutical industry which are enforced by the FDA. Under USP 24, General Chapters, Dissolution (711), the shaft must be positioned such that its centerline is not more than 2 mm at any point from the vertical axis of the vessel, and such that the paddle or basket (typically mounted to the lower end of the shaft) be positioned at 25 mm ±2 mm from the bottom of the vessel.

Various hand-held devices have been utilized to carry out the measurements required to determine whether a shaft is positioned in a dissolution test vessel in compliance with the above-cited guidelines. Rulers, machinist calipers and micrometers, and pass/fail fixtures typify such devices and are known to persons skilled in the art. It is readily apparent to such skilled persons that operation of these devices requires a great deal of manual handling, with critical specifications largely determined by sight and feel. Conventional shaft measurement devices therefore engender an unacceptably high risk of error. There accordingly exists a long felt need for improved apparatus and methods for determining the position of a shaft installed in the vessel of a dissolution testing station.

DISCLOSURE OF THE INVENTION

In accordance with the present invention, an apparatus is mountable to a shaft disposed within a vessel and is adapted for measuring the magnitude by which the centerline of the shaft is offset from the central axis of the vessel. The apparatus comprises a housing and a plunger slidably mounted to the housing. The plunger has an outer section extending radially outwardly beyond a wall of the housing, and means such as a spring for biasing the plunger radially outwardly. A transducer is operatively mounted to the housing. The transducer is adapted to encode positions of the plunger and to produce an electrical signal proportional to a change in position resulting from displacement of the plunger. Means such as data lines are provided for transferring the signal to means such as a microprocessor for interpreting the signal.

In another embodiment according to the present invention, an apparatus is mountable to a shaft having a paddle or basket disposed within a vessel. The vessel has a central axis and a hemispherical end region. The apparatus is adapted for measuring the distance from a distal surface of the paddle or basket to a lowermost point on the inside surface of the hemispherical end region. The apparatus comprises a housing and a plunger slidably mounted to the housing. The plunger has an outer section extending outwardly beyond a wall of the housing, and means such as a spring for biasing the plunger outwardly. An end portion extends transversely from the plunger beneath the housing and is substantially centered about a central portion of the housing. A transducer is operatively mounted to the housing. The transducer is adapted to encode positions of the plunger and to produce an electrical signal proportional to a change in position resulting from displacement of the plunger. Means such as data lines are provided for transferring the signal to means such as a microprocessor for interpreting the signal.

In another embodiment according to the present invention, a system is provided for determining the location of a rotatable shaft in relation to a vessel mounted to a rack of a dissolution testing station. The shaft has a first end mounted to the testing station above the vessel, a second end disposed within the vessel and an operative component secured to the second end. The system comprises a housing including means such as a resilient clip and groove for removably mounting the housing to the shaft, and a plunger slidably mounted to the housing. The plunger has an outer section extending radially outwardly beyond a wall of the housing and extendable to an inside lateral surface of the vessel, and has means such as a spring for biasing the plunger radially outwardly. A transducer is operatively mounted to the housing. The transducer is adapted to encode positions of the plunger, and to produce an electrical signal proportional to a distance from a reference position to an extended position at which the plunger is in contact with the inside lateral surface of the vessel. Means such as data lines are provided for transferring the signal to means such as a microprocessor for interpreting the signal.

In another embodiment according to the present invention, a system is provided for determining the location of a rotatable shaft in relation to a vessel. The vessel has a central axis and a hemispherical end region, and is mounted to a rack of a dissolution testing station. The shaft has a first end mounted to the testing station above the vessel, a second end disposed within the vessel and an operative component such as a paddle or basket secured to the second end. The system comprises a spherical object removably disposed in a lowermost point on an inside surface of the hemispherical end region of the vessel. A housing includes means such as a resilient clip or groove for removably mounting the housing to the shaft. A plunger is slidably mounted to the housing. The plunger has an outer section extending beyond a wall of the housing and extendable to the spherical object, and has means such as a spring for biasing the plunger outwardly. An end portion has an upper surface and a lower surface, and extends transversely from the plunger and between the operative component and the spherical object.

A transducer is operatively mounted to the housing. The transducer is adapted to encode positions of the plunger, and to produce an electrical signal proportional to a distance from a reference position at which the top surface of the end portion of the plunger is biased against the operative component to an extended position at which the lower surface is in contact with the spherical object. Means such as data lines are provided for transferring the signal to means such as a microprocessor for interpreting the signal.

In another object according to the present invention, a system is provided for determining the location of a shaft in relation to a vessel in which the shaft is disposed. The vessel has a central axis and a hemispherical end region. The system comprises a shaft offset measurement device which includes a first housing and a first plunger slidably mounted to the first housing. The first plunger has an outer section extending radially outwardly beyond a wall of the first housing and means such as a spring for biasing the first plunger radially outwardly. A first transducer is operatively mounted to the first housing. The first transducer is adapted to encode positions of the first plunger and to produce a first electrical signal proportional to a change in position resulting from displacement of the first plunger.

The system further comprises a shaft height measurement device which includes a second housing and a second plunger slidably mounted to the second housing. The second plunger has an outer section extending outwardly beyond a wall of the second housing, and means such as a spring for biasing the second plunger outwardly. An end portion extends transversely from the second plunger beneath the second housing and is substantially centered about a central portion of the second housing. A second transducer is operatively mounted to the second housing. The second transducer is adapted to encode positions of the second plunger and to produce a second electrical signal proportional to a change in position resulting from displacement of the second plunger.

The system further comprises a console including logic means such as a microprocessor for effecting interpretations of the first and second electrical signals and means such as an LCD display for displaying the interpretations in human-readable form. Means such as data lines are provided for transferring the first and second electrical signals to the logic means.

In another embodiment according to the present invention, an apparatus is adapted for measuring the magnitude by which the centerline of a shaft is offset from the central axis of a vessel in which the shaft is disposed, and for measuring the distance from a distal end of the shaft to the lowermost point on an inside surface of a hemispherical end region of the vessel. The apparatus comprises a mounting assembly, a lateral plunger slidably mounted to the mounting assembly, a lateral transducer operatively disposed with respect to the mounting assembly and to the lateral plunger, a vertical plunger slidably mounted to the mounting assembly, and a vertical transducer operatively disposed with respect to the mounting assembly and to the vertical plunger.

The lateral plunger has means such as a spring for biasing the lateral plunger radially outwardly. The lateral transducer is adapted to encode positions of the lateral plunger and to produce an electrical signal proportional to a change in position resulting from displacement of the lateral plunger. The vertical plunger has means such as a spring for biasing the vertical plunger downwardly with respect to the mounting assembly, and includes an upper end portion extending transversely from the vertical plunger. The vertical transducer is adapted to encode positions of the vertical plunger and to produce an electrical signal proportional to a change in position resulting from displacement of the vertical plunger. Means such as data lines are provided for transferring the signals produced respectively by the lateral and vertical transducers to means for interpreting the signals. The signal interpreting means can include a console with which the signal transferring means communicates, wherein the console has logic means such as a microprocessor for effecting interpretations of the signals and means such as an LCD display for displaying the interpretations in human-readable form.

The present invention also provides methods for determining the position of a shaft installed in a vessel with respect to the central axis of the vessel and/or lowermost point inside the vessel.

Accordingly, a method is provided for measuring the amount by which the centerline of a shaft is offset from the central axis of a vessel in which the shaft is to be disposed, comprising the following steps. A measurement device which includes a radially outwardly biased plunger is mounted to the shaft. The plunger has a settable zero reference position. The shaft is inserted into the vessel at a normal operating position of the shaft, wherein a distal end of the plunger is in contact with a lateral inside surface of the vessel at a first distal plunger position. A first displaced plunger position is defined as a position on the plunger located a distance by which the plunger has moved in relation to the zero reference position, the distance being equal a first displacement magnitude.

The displacement magnitudes are measured by encoding the displaced plunger position and interpreting the displaced plunger position in relation to the zero reference position, wherein the displacement magnitudes determine the shaft centerline offset amount. A value for the shaft centerline offset amount is calculated based on the measured first displacement magnitudes. Finally, a signal is produced which is indicative of the shaft centerline offset amount.

Accordingly, another method is provided wherein a distal end of the plunger position is in contact with a lateral inside surface of the vessel at a first distal plunger position. This first displaced plunger position is reset to the zero reference position. The shaft is then rotated one full revolution while continuously sampling the displacement of the plunger position is defined as a position on the plunger located a distance by which the plunger has moved in relation to the zero reference position, the distance being equal to the displacement magnitude from this continuous sampling, the lowest and the largest displacement magnitudes are kept.

Another method according to the present invention is for measuring a shaft height, which is defined as the distance between the distal end of a shaft and the inside lowermost surface of a hemispherical end region of a vessel in which the shaft is to be disposed. The method comprises the following steps. A measurement device which includes a downwardly biased plunger is mounted to the shaft. The plunger includes an end portion. The end portion extends below the shaft and has a predetermined end portion height. A zero reference position of the plunger is defined by urging the end portion against the distal end of the shaft. The zero reference position is encoded. The inside lowermost surface of the hemispherical end region of the vessel is located by inserting a spherical object having a predetermined diameter into the vessel. The shaft is inserted into the vessel at a normal operating position of the shaft, permitting the end portion of the plunger to contact the spherical object.

A displaced plunger position is defined as a position on the plunger located a distance by which the plunger has moved in relation to the zero reference position in order to contact the spherical object, the distance being equal to a displacement magnitude. The displacement magnitude is measured by encoding the displaced plunger position and interpreting the displaced plunger position in relation to the zero reference position, wherein the sum of a predetermined constant plus the displacement magnitude is proportional to the shaft height. A value for the shaft height is calculated based on the measured displacement magnitude. A signal is produced which is indicative of the shaft height.

A further method according to the present invention is for measuring the amount by which the centerline of a shaft is offset from the central axis of a vessel in which the shaft is to be disposed, and for measuring a shaft height defined as the distance between the distal end of the shaft and the inside lowermost surface of a hemispherical end region of the vessel. The method comprises the following steps. The inside lowermost surface of the hemispherical end region of the vessel is located by inserting a spherical object into the vessel. A measurement device is mounted over the vessel. The measurement device includes a lateral plunger and a vertical plunger. The vertical plunger includes an end portion. The shaft is inserted into the vessel at a normal operating position of the shaft.

A distal end of the lateral plunger is permitted to contact a lateral inside surface of the vessel. A displaced lateral plunger position is defined as a position on the lateral plunger located a lateral distance by which the lateral plunger has moved in relation to a predetermined zero reference position of the lateral plunger, the lateral distance being equal to a lateral displacement magnitude. The lateral displacement magnitude is measured by encoding the displaced lateral plunger position and interpreting the displaced lateral plunger position in relation to the zero reference position of the lateral plunger, wherein the lateral displacement magnitude determines the shaft centerline offset amount. A value for the shaft centerline offset amount is calculated based on the measured lateral displacement magnitude. A signal is produced which is indicative of the shaft centerline offset amount.

The end portion of the vertical plunger is permitted to contact the spherical object. A displaced vertical plunger position is defined as a position on the vertical plunger located a vertical distance by which the vertical plunger has moved in relation to a predetermined zero reference position of the plunger, the vertical distance being equal to a vertical displacement magnitude. The vertical displacement magnitude is measured by encoding the displaced vertical plunger position and interpreting the displaced vertical plunger position in relation to the zero reference position of the vertical plunger, wherein the vertical displacement magnitude determines the shaft height. A value for the shaft height is calculated based on the measured vertical displacement magnitude. A signal is produced which is indicative of the shaft height.

It is therefore an object of the present invention to provide an apparatus for measuring the amount by which the centerline of a shaft disposed in a vessel is offset from the central vertical axis of the vessel.

It is another object of the present invention to provide an apparatus for measuring the height of such shaft above the lowermost inside point of the vessel.

It is a further object of the present invention to provide an apparatus for controlling the process by which the shaft centerline offset amount and shaft height are measured, and for expressing the results of such process using peripheral devices.

It is yet another object of the present invention to provide improved methods for determining accurate values for the shaft centerline offset amount and shaft height.

Some of the objects of the invention having been stated hereinabove, other objects will become evident as the description proceeds, when taken in connection with the accompanying drawings as best described hereinbelow.

BRIEF DESCRIPTION OF THE DRAWINGS

FIGS. 7A and 7B are front and rear elevation views, respectively, of a shaft height measurement device mounted to a shaft within a vessel according to the present invention;

FIGS. 10A and 10B are perspective views of a combined shaft centerline offset and height measurement device according to the present invention;

DETAILED DESCRIPTION OF THE INVENTION

Figure 1:
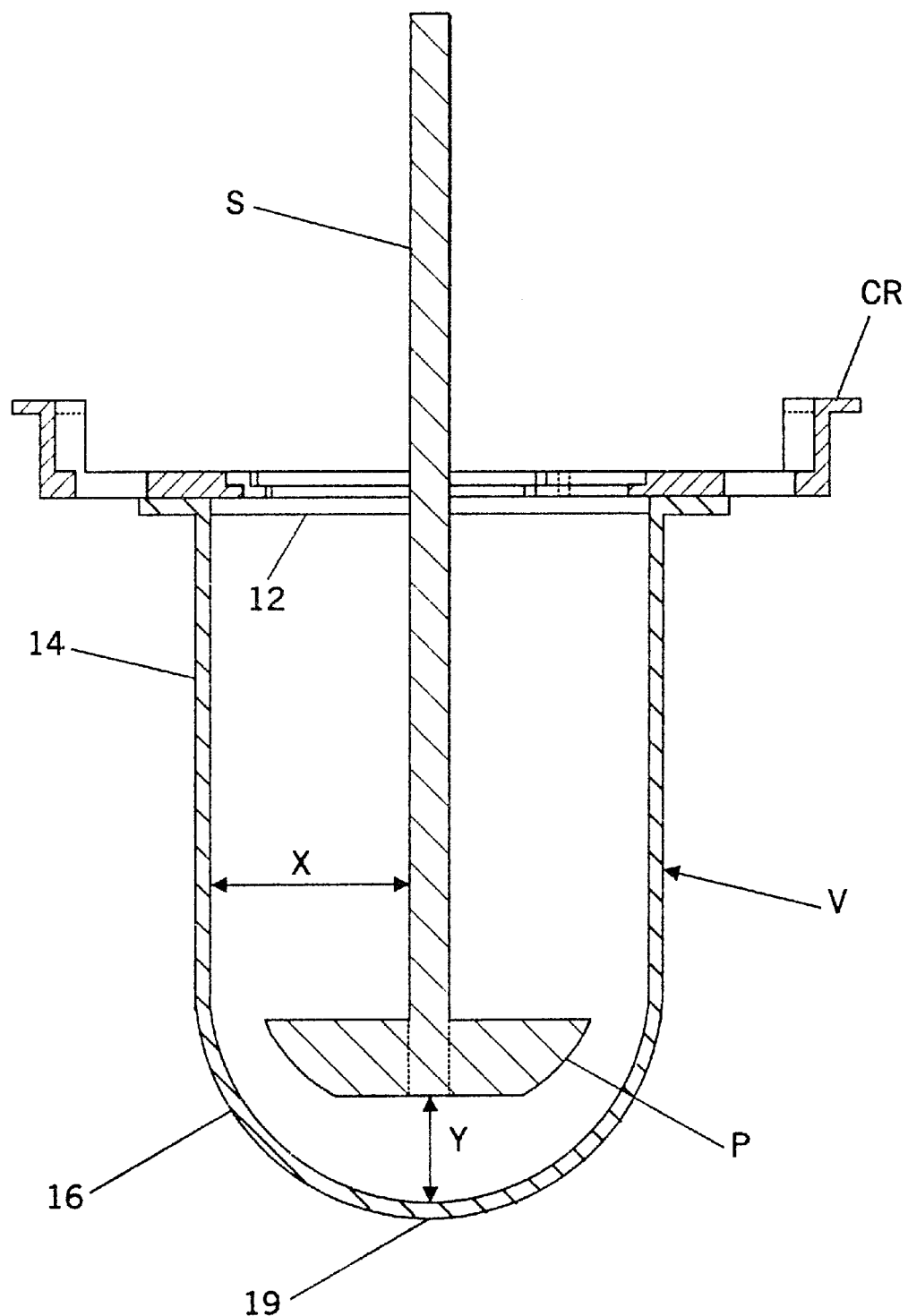
FIG. 1 is a cross-sectional view of a paddle shaft installed in a vessel in which the present invention is implemented.
Figure 2:
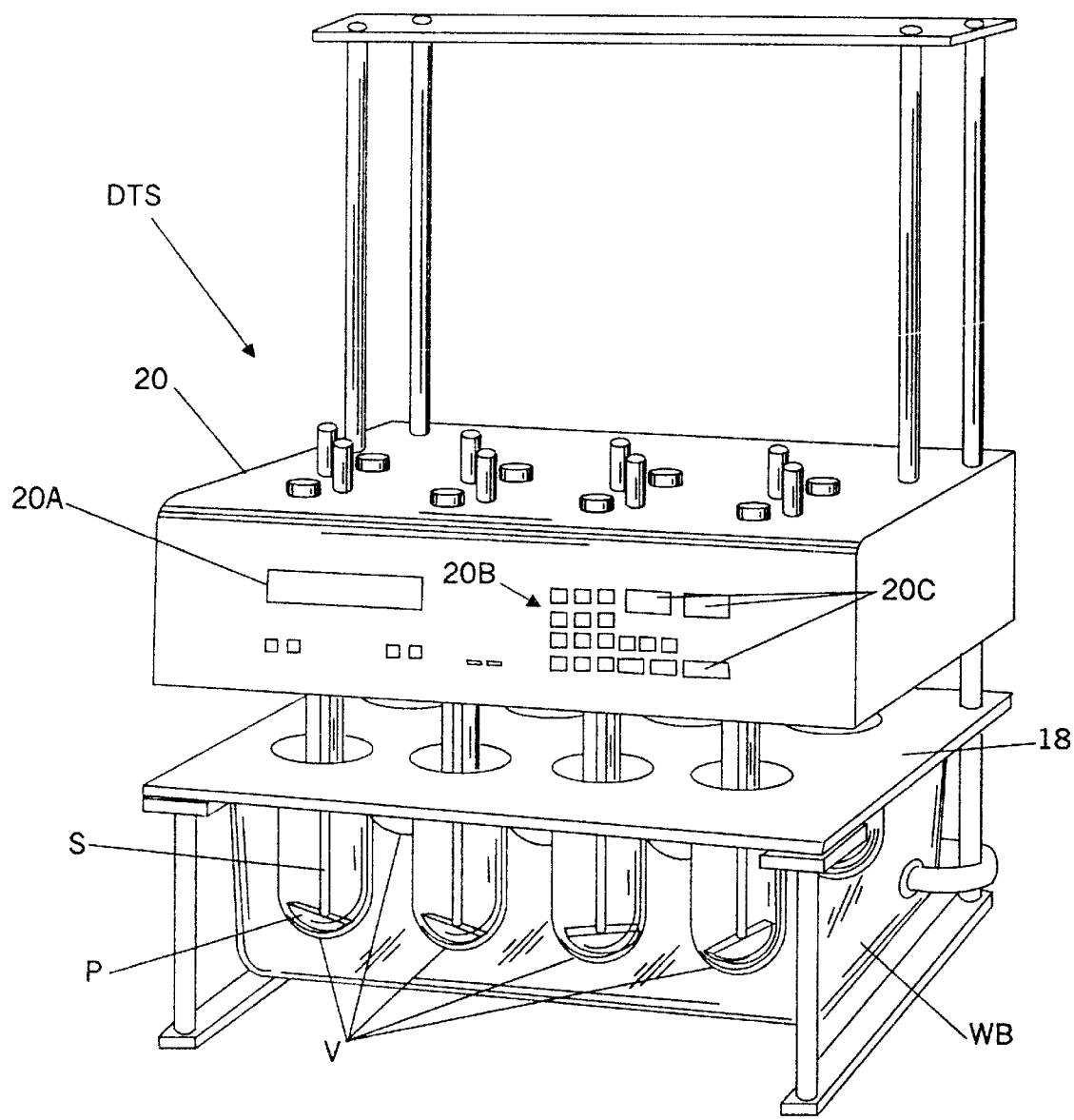
FIG. 2 is a perspective view of a dissolution testing station in which the present invention is implemented.

FIG. 1 illustrates a typical vessel V employed in a dissolution testing station, while FIG. 2 illustrates one such testing station generally designated DTS. Vessel V has an open upper end 12, a lateral side region 14, and a hemispherical end region 16. A plurality of vessels V (typically 6 or 8) are mounted in a rack 18 of dissolution testing station DTS for high-throughput testing. Each vessel V is centered and locked into position on rack 18 with the aid of a vessel centering ring CR (not shown in FIG. 2). Dissolution testing station DTS includes, among other components, a water bath WB for temperature control of vessels V and a programmable systems control module 20 having peripheral elements such as an LCD display 20A, a keypad 20B, and individual readouts 20C. A shaft S provided with a paddle or basket P may be inserted into each vessel V. One or more spindle motors (not shown) housed within control module 20 drive the rotation of shafts S through a chuck (not shown) or equivalent coupling means. Referring specifically to FIG. 1, the parameters of shaft position relative to vessel V sought to be determined are shaft centerline offset determined by shaft distance x, and shaft or paddle height y. The present invention described in detail below has been found by applicants to measure these parameters accurately to within 0.1 mm.

Figure 3A:
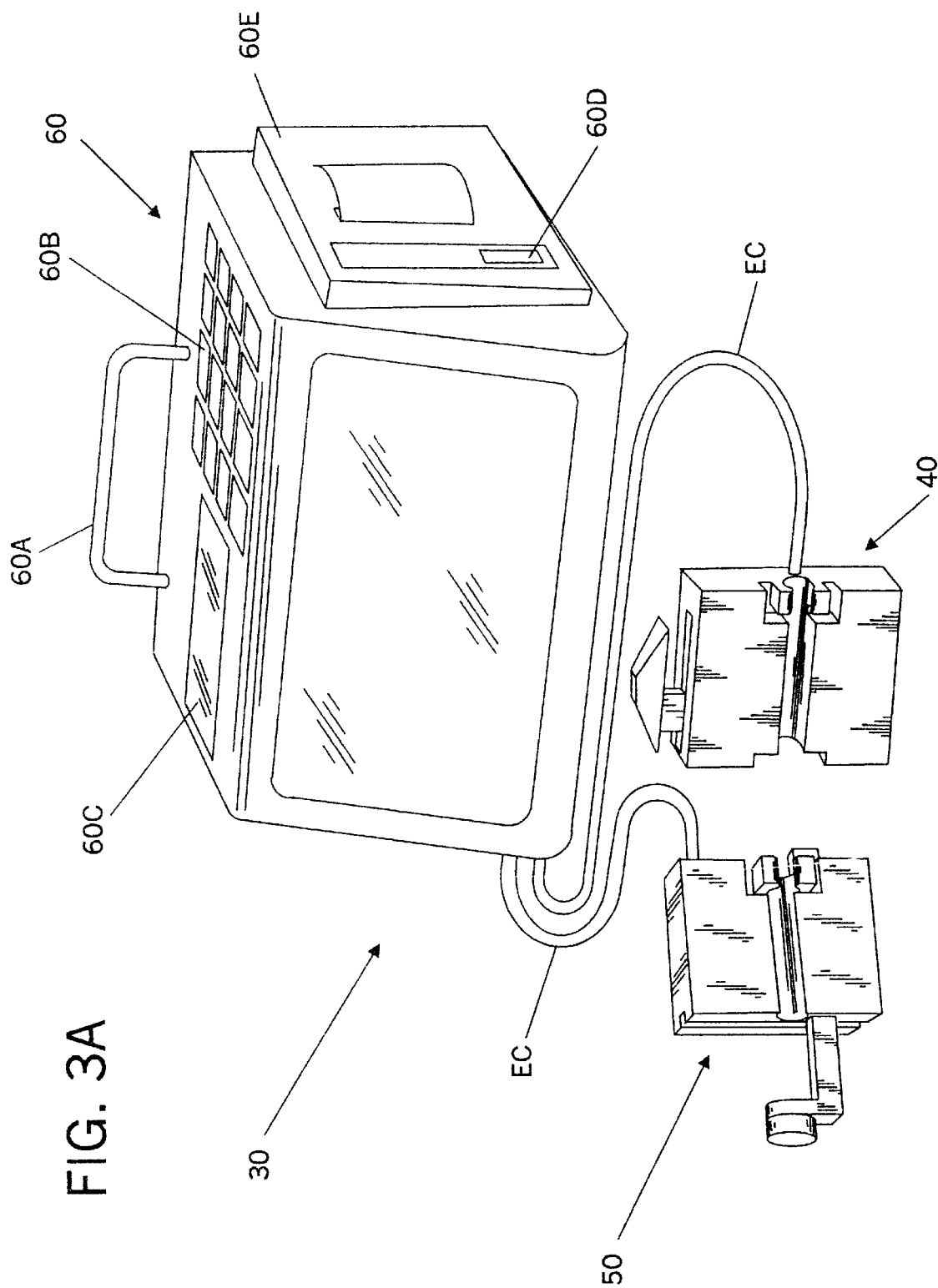
FIG. 3A is a perspective view of a shaft centerline offset and height measurement system according to the present invention.
Figure 3C:
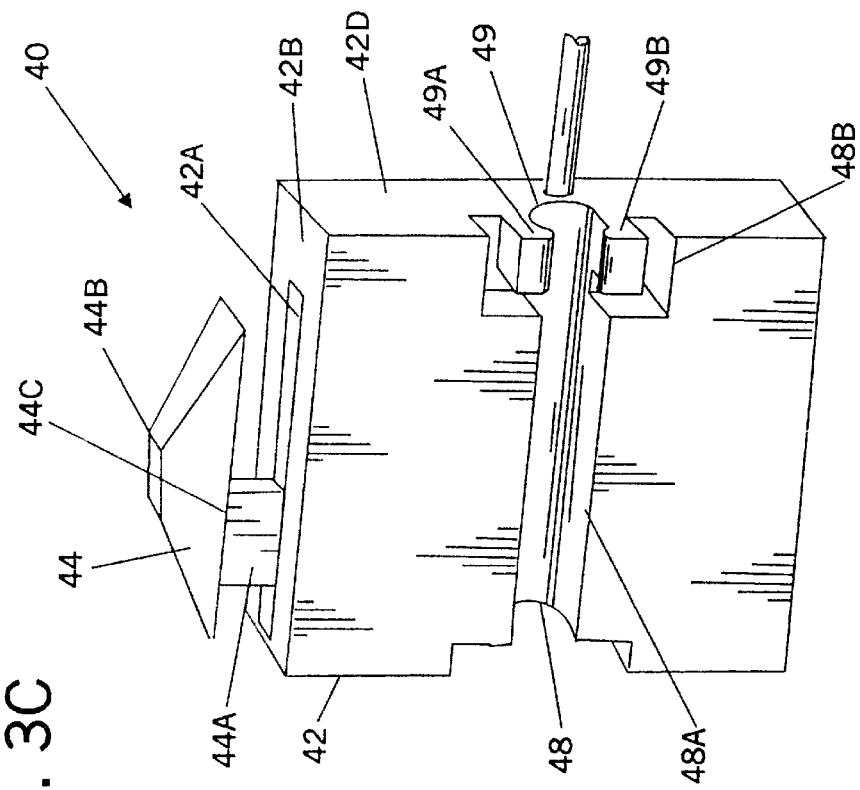
FIG. 3C is a perspective view of a shaft centerline offset measurement device according to the present invention.
Figure 3B:
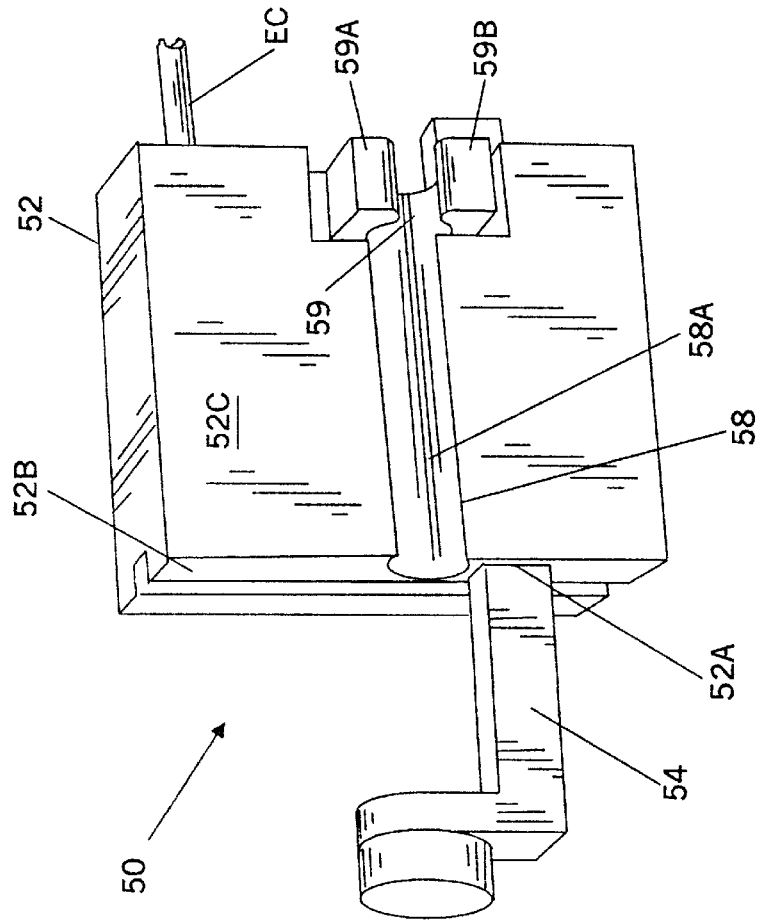
FIG. 3B is a perspective view of a shaft height measurement device according to the present invention.

FIGS. 3A through 3C show a shaft centerline offset and height measurement system according to the present invention and generally designated 30. Primary components of measurement system include a shaft centerline offset measurement device generally designated 40, a height measurement device generally designated 50, and a control/display console generally designated 60. Control/display console 60 is portable and thus includes a handle 60A. A keypad 60B is provided for inputting commands, calibration data, and the like. Results derived from measurements taken by centerline offset and height measurement devices 40, 50 are transferred through electrical conduits EC and may be displayed at display screen 60C, which is preferably an LCD type display. Alternatively, these results may be sent through a communication port 60D such as an RS 232 port to another peripheral such as a remote computer. Control/display console 60 can also be equipped with an on-board dot-matrix printer 60E. In addition, control/display console 60 includes a decoder chip adapted for decoding signal received from transducers, a CPU for performing calculations and other computing functions, a memory register, and other associated logic components and circuitry (not shown). A suitable decoder chip is a quadrature decoder available from HEWLETT PACKARD as model designation HCTL-2016. A suitable CPU is a micro controller unit available from PHILLIPS as model designation 87C52.

Centerline offset measurement device 40 is illustrated in more detail in FIGS. 3C and 4A through 4D. Height measurement device 50 is illustrated in more detail in FIGS. 3B and 5A through 5D.

Figure 4A:
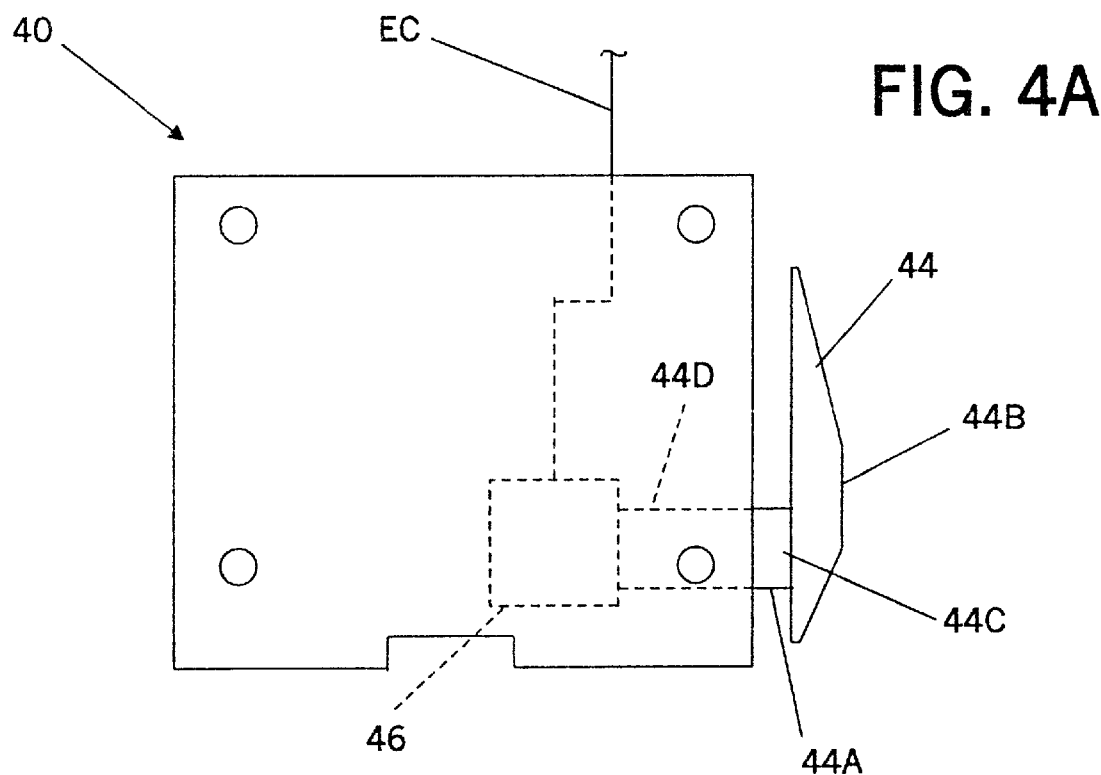
FIG. 4A is a front elevation view of the shaft centerline offset measurement device in FIG. 3C.

Referring particularly to FIGS. 3C and 4A, centerline offset measurement device 40 includes a housing 42, a lateral plunger 44, and a horizontally-oriented sensor or transducer 46 (indicated schematically in FIG. 4A by phantom lines). Preferably, both lateral plunger 44 and transducer 46 are mounted within housing 42. Lateral plunger 44 is movably mounted to housing 42 by conventional means, such that lateral plunger 44 can slide inwardly and outwardly with respect to housing 42. An outer section 44A of lateral plunger 44 extends outside housing 42 through a hole 42A in a wall 42B of housing 42. Means such as a spring (not shown) is provided to interface with lateral plunger 44 and housing 42 and to impart a biasing force to lateral plunger 44 in a radially outward direction away from housing 42. Preferably, an arrow-shaped plunger head 44B is provided at a distal end 44C of lateral plunger 44 for a purpose described hereinbelow. Means such as an electrical conduit EC containing lead wires is provided for transferring signals generated by transducer 46.

Transducer 46 serves to measure a change in lateral position of lateral plunger 44 by converting a sense of the physical change in such position to an electronic signal representative of the magnitude of such change. For this purpose, transducer 46 is preferably an optical linear encoder module such as model designation HEDS 9200 R00 available from HEWLETT PACKARD. Transducer 46 operates in conjunction with a code strip (not shown) in a manner typical of optical encoders. Because transducer 46 is to measure positional changes of lateral plunger 44, the code strip is mounted to an inner section 44D of lateral plunger 44 in the vicinity of transducer 46. Hence, as lateral plunger 44 moves, the code strip moves with respect to transducer 46. As the code strip passes by transducer 46, transducer 46 optically reads and counts lines on the code strip. The number of lines counted is correlated to a magnitude by which lateral plunger 44 has moved from an initial reference position. Alternatively, transducer 46 could be mounted to lateral plunger 44 and the code strip fixedly secured within housing 42.

Figure 4B:
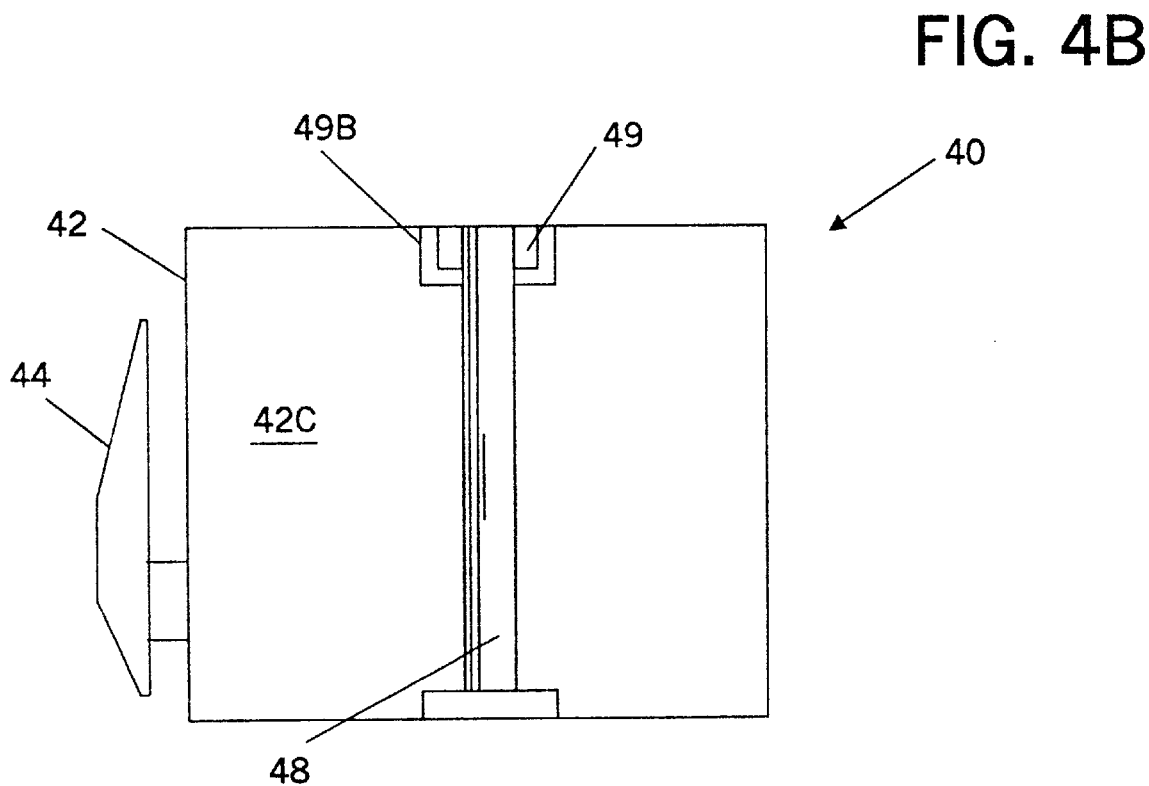
FIG. 4B is a rear elevation view of the shaft centerline offset measurement device in FIG. 3C.
Figure 4C:
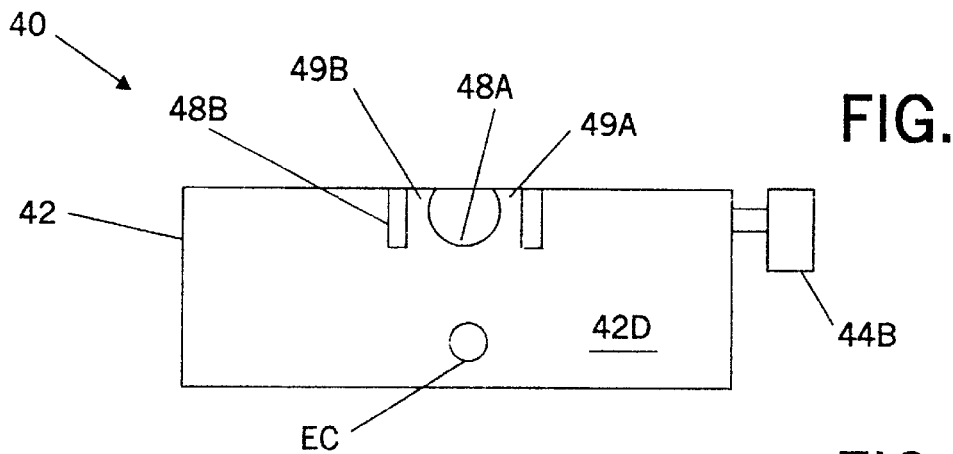
FIG. 4C is a top plan view of the shaft centerline offset measurement device in FIG. 3C.
Figure 4D:
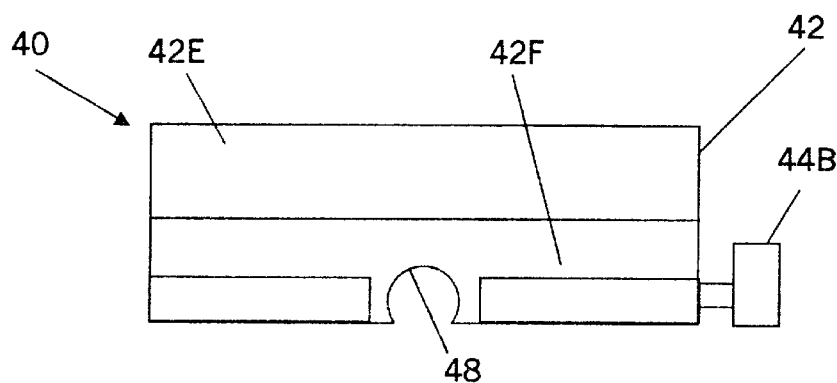
FIG. 4D is a bottom plan view of the shaft centerline offset measurement device in FIG. 3C.
Figure 6B:
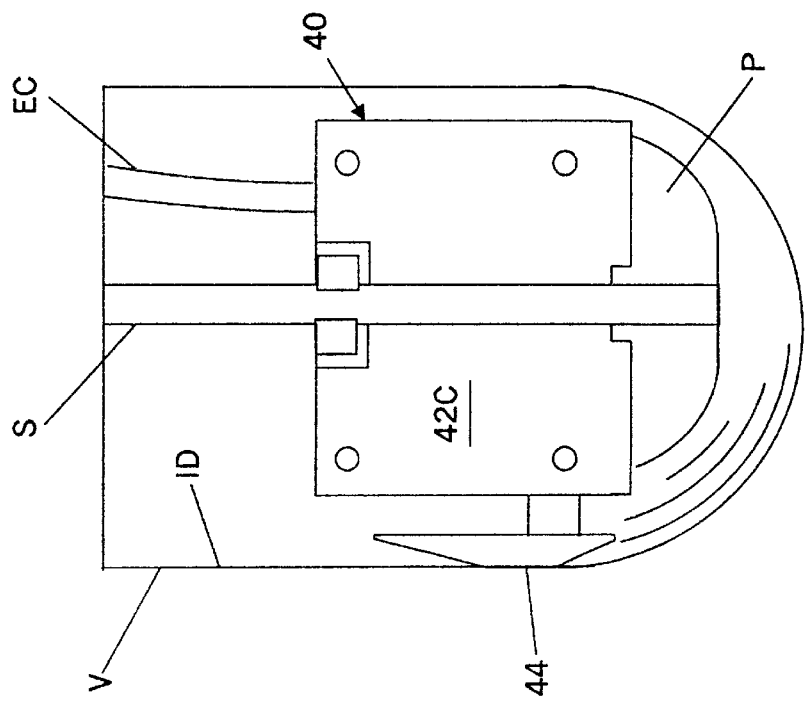
FIGS. 6A and 6B are front and rear elevation views, respectively, of a shaft centerline offset measurement device mounted to a shaft within a vessel according to the present invention.
Figure 6A:
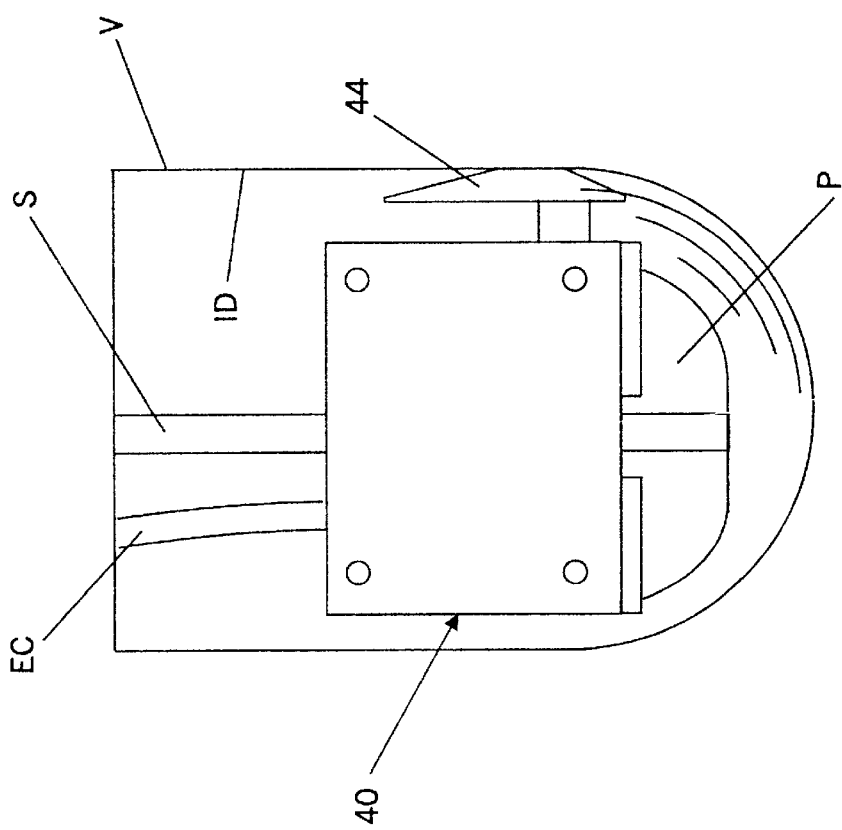

Referring to FIGS. 3C, 4B and 4C, a longitudinal recess 48 is formed in a rear face 42C of housing 42 by a recess wall 48A. Preferably, recess wall 48A has a cylindrical profile to better accommodate the contour of shaft S. In an upper section 48B of longitudinal recess 48 proximate to a top face 42D of housing 42, a clip-like member 49 is provided to assist the secure mounting of shaft centerline offset measurement device 40 to shaft S. Clip-like member 49 includes a pair of resilient prongs 49A and 49B. In addition, a bottom face 42E of housing 42 may be configured to conform to the specific type of operative component, e.g., paddle or basket P, carried on shaft S in order to further assist in mounting thereto. Thus, in the exemplary embodiment shown in FIG. 4D, bottom face 42E includes a groove 42F that enables housing 42 to straddle paddle P when mounted to shaft S. FIGS. 6A and 6B show centerline offset measurement device 40 mounted to shaft S and shaft S installed in vessel V.

Figure 5C:
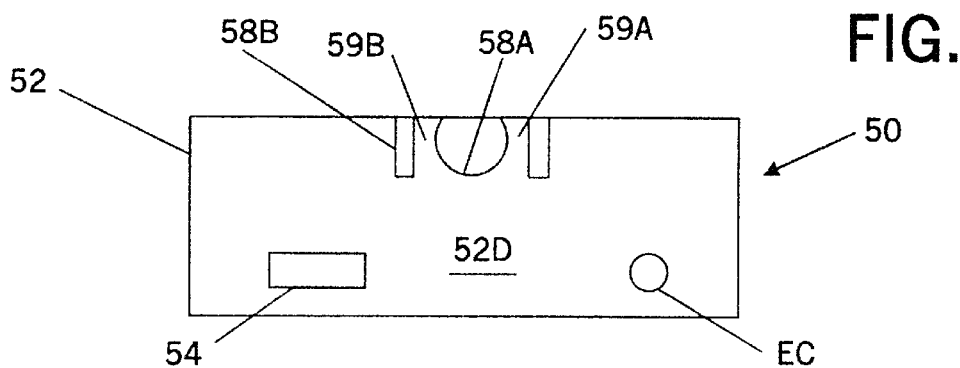
FIG. 5C is a top plan view of the shaft height measurement device in FIG. 3B.
Figure 5D:
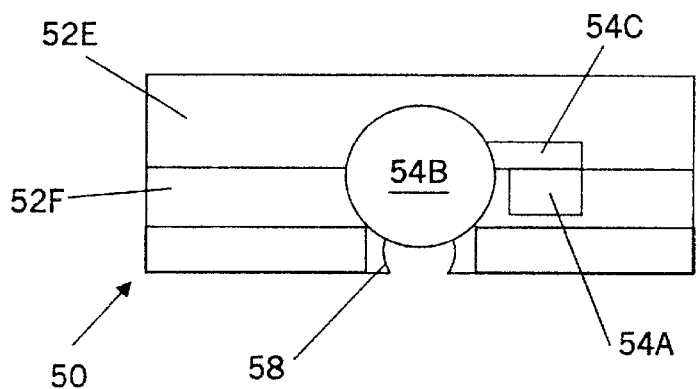
FIG. 5D is a bottom plan view of the shaft height measurement device in FIG. 3B.
Figure 5A:
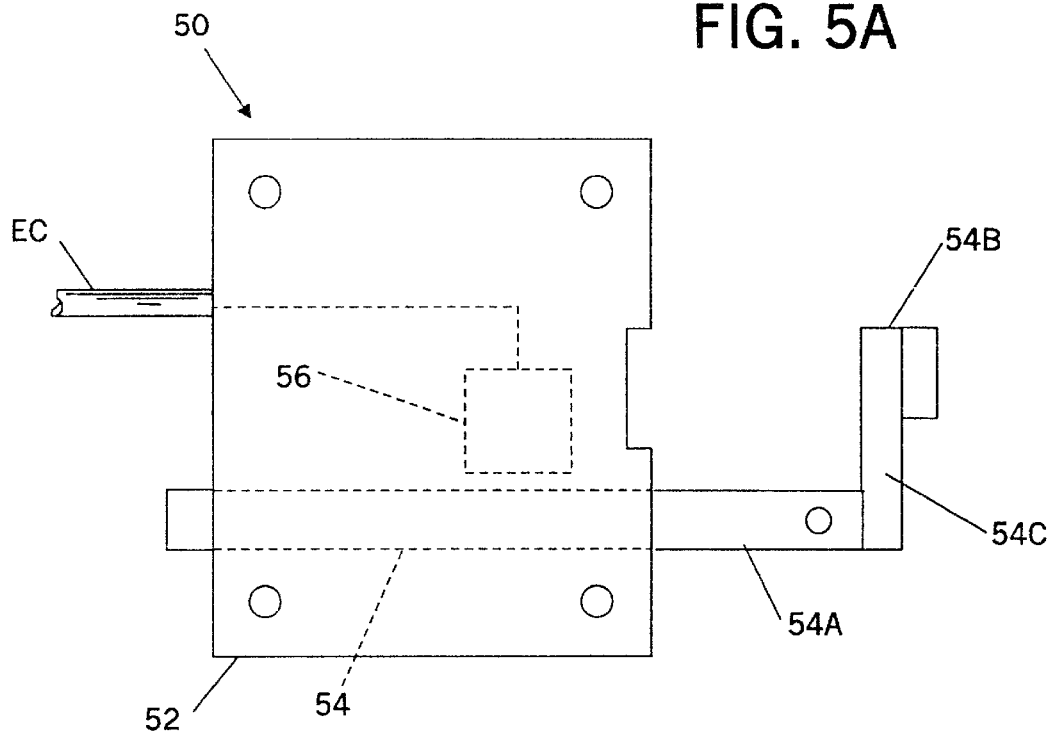
FIG. 5A is a front elevation view of the shaft height measurement device in FIG. 3B.

Referring particularly to FIGS. 3B and 5A, height measurement device 50 includes a housing 52, a vertical plunger 54, and a vertically-oriented sensor or transducer 56 (indicated schematically in FIG. 5A by phantom lines). As in the case of centerline offset measurement device 40, both vertical plunger 54 and transducer 56 are preferably mounted within housing 52. Vertical plunger 54 is movably mounted to housing 52 by conventional means, such that vertical plunger 54 can slide inwardly and outwardly with respect to housing 52. An outer section 54A of vertical plunger 54 extends outside housing 52 through a hole 52A in a wall 52B of housing 52. Means such as a spring (not shown) is provided to interface with vertical plunger 54 and housing 52 and to impart a biasing force to vertical plunger 54 in a downward direction away from housing 52. An end portion 54B is attached to vertical plunger 54 in offset relation thereto by means of an intermediate member 54C.

Accordingly, when height measurement device 50 is mounted to shaft S, vertical plunger 54 is situated in parallel relation to shaft S and end portion 54B is centrally disposed beneath shaft S and its operative component P. The purpose of end portion 54B is described hereinbelow. Finally, means such as an electrical conduit EC containing lead wires is provided for transferring signals generated by transducer 56.

In a manner analogous to that respecting centerline offset measurement device 40, transducer 56 serves to measure a change in vertical position of vertical plunger 54 by converting a sense of the physical change in such position to an electronic signal representative of the magnitude of such change. Consequently, transducer 56 specified for height measurement device 50 is the same or similar unit as transducer 46 specified for centerline offset measurement device 40, as well as the associated code strip which preferably is mounted to vertical plunger 54.

Figure 5B:
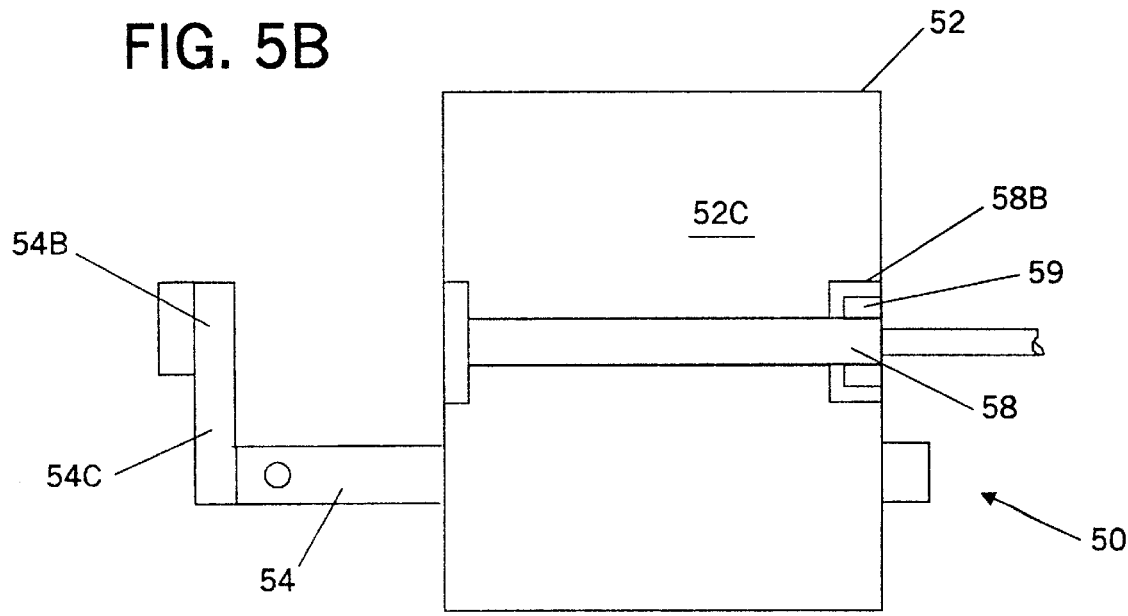
FIG. 5B is a rear elevation view of the shaft height measurement device in FIG. 3B.

Referring to FIGS. 3B, 5B and 5C, means are provided for mounting height measurement device 50 to shaft S similar to that respecting centerline offset measurement device 40. That is, a longitudinal recess 58 is formed in a rear face 52C of housing 52 by a cylindrically-profiled recess wall 58A. A clip-like member 59 including a pair of resilient prongs 59A and 59B is disposed in an upper section 58B of longitudinal recess 58 proximate to a top face 52D of housing 52. In addition, a bottom face 52E of housing 52 includes a groove 52F or other means for improving the securement of height measurement device 50 to shaft S provided with paddle P or the like, as shown in FIG. 5D. FIGS. 7A and 7B show height measurement device 50 mounted to shaft S and shaft S installed in vessel V.

The operation of shaft centerline offset and height measurement system 30 will now be described with particular reference to FIGS. 3A, 6A, 6B, 7A, 7B, 8A through 8C, and 9. By way of example, an indication of centerline offset is obtained before an indication of shaft or paddle height is obtained.

Referring to FIGS. 6A and 6B, the operation of centerline shaft measurement device 40 will first be described. Centerline offset measurement device 40 is affixed to shaft S. Shaft S is then lowered into vessel V at a normal operating position for shaft S. Because lateral plunger 44 is preferably biased radially outwardly, the tapered edges that comprise arrow-shaped plunger head 44B assist in installing and removing shaft S from vessel V when centerline offset measurement device 40 is mounted to shaft S. After shaft S is disposed in its normal operating position, a distal end (which in the present exemplary embodiment corresponds to the outermost surface of plunger head 44B) of outwardly biased lateral plunger 44 is in contact with a lateral inside surface ID of vessel V.

At this point, assuming shaft S is offset from the true central vertical axis of vessel V, lateral plunger 44 will have displaced laterally with respect to a zero reference position. At this plunger position, lateral plunger 44 will have displaced a distance equal to a displacement magnitude. This displacement magnitude is evident by the change in position of the code strip mounted to lateral plunger 44. Transducer 46 encodes the displaced position of the code strip, and thus the displaced position of lateral plunger 44, and sends the encoded signal to control/display console 60 (see FIG. 3A), which decodes, stores, and processes the signal.

The displacement magnitude measured is one indication of the amount by which shaft S is offset from the central axis of vessel V. This displacement magnitude alone, however, is not necessarily a good indication when one considers that the position of lateral plunger 44 will change when lateral plunger 44 is disposed at other distal plunger positions on the circumference of lateral inside surface ID of vessel V. Accordingly, more precision can be achieved by employing transducer 46 to sample a plurality of displaced plunger positions. These displaced plunger positions are obtained when lateral plunger 44 is rotated to define a plurality of distal plunger positions located on the circumference of lateral inside surface ID. By doing so, a calculation of the centerline offset amount can be based on a plurality of displacement magnitudes measured by transducer 46 at different circumferential locations on lateral inside surface ID.

Figure 8A:
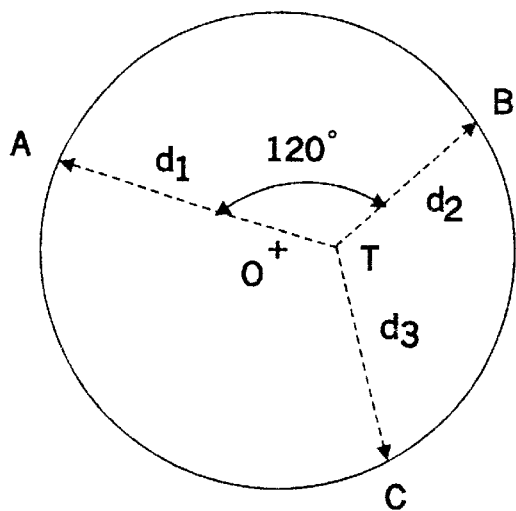
FIGS. 8A, 8B and 8C are geometric views illustrating a method for calculating the offset amount of the centerline of a shaft according to the present invention.
Figure 8B:
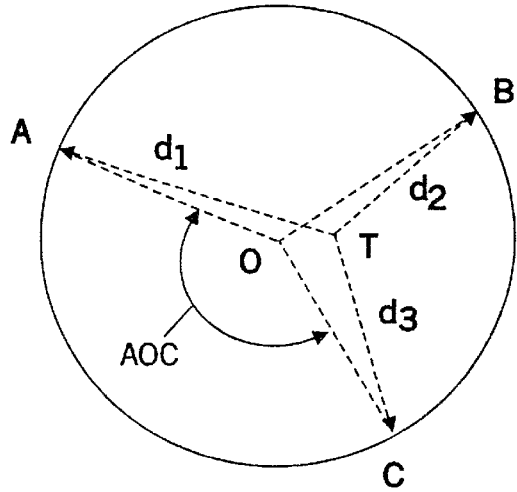
Figure 8C:
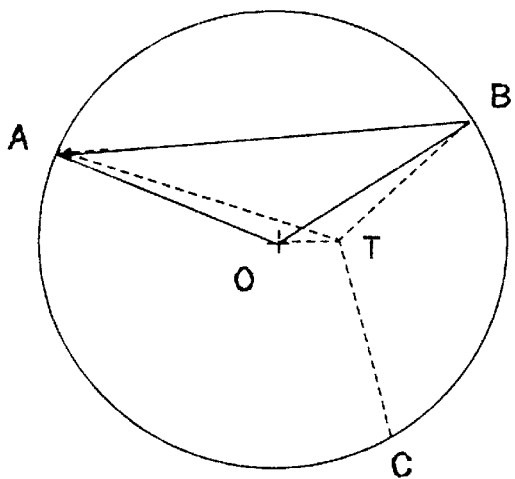

Referring to FIGS. 8A through 8C, lateral inside surface ID is assumed to be a perfect circle ABC for purposes of calculation and has a center O through which central axis of vessel V runs. The centerline of the shaft S is represented by a point T, thus illustrating that shaft S is clearly not in alignment with the central axis of vessel V. Shaft S with centerline offset measurement device 40 mounted thereto is inserted into vessel V as described above, at which time distal end or plunger head 44B of lateral plunger 44 contacts lateral inside surface ID at a first distal plunger position A. The distance by which lateral plunger 44 is displaced at this time is encoded by transducer 46 and stored in control/display console 60 as a first displacement magnitude. After the first displacement magnitude is measured, second and third displacement magnitudes are likewise measured by respectively rotating lateral plunger 44 120° (or one-third of a revolution around lateral inside surface ID) to a second distal plunger position B and another 120° to a third distal plunger position C.

Lateral plunger 44 can be rotated by manually rotating housing 42 around shaft S or by rotating shaft S itself. In order to aid in locating the 120° positions, indicator marks (not shown) could be provided, for instance, on vessel centering ring CR (see FIG. 1). Nevertheless, the method described herein will give an accurate indication of centerline offset even if readings are taken at plunger positions that deviate approximately ±5° from the 120° positions.

Referring to FIG. 8A, a radial distanced, along lateral plunger 44 from centerline T to first distal plunger position A, a radial distance $d_2$ along lateral plunger 44 from centerline T to second distal plunger position B, and a radial distance $d_3$ along lateral plunger 44 from centerline T to third distal plunger position C are obtained. Radial distances $d_1$ $d_2$ and $d_3$ can be derived in a variety of ways, such as by taking a value representing some constant plunger length and adjusting that value by taking into account the measured first, second and third displacement magnitudes, respectively. A chordal distance AB between first and second distal plunger positions A, B, a chordal distance AC between first and third distal plunger positions A, C and a chordal distance BC between second and third distal plunger positions B, C are then calculated respectively according to the following equations derived from the law of cosines:

$$AB = \sqrt{(d_1)^2 + (d_2)^2 - 2 \cdot d_1 \cdot d_2 \cdot \cos\left(\frac{2 \cdot \pi}{360} \cdot 120\right)}$$

$$AC = \sqrt{(d_1)^2 + (d_3)^2 - 2 \cdot d_1 \cdot d_3 \cdot \cos\left(\frac{2 \cdot \pi}{360} \cdot 120\right)}$$

-continued $$BC = \sqrt{(d_3)^2 + (d_2)^2 - 2 \cdot d_3 \cdot d_2 \cdot \cos\left(\frac{2 \cdot \pi}{360} \cdot 120\right)}$$

Next, a theoretical radius R for circle ABC based on chordal distances AB, AC, and BC is calculated according to the following equation:

$$R = \frac{AB \cdot AC \cdot BC}{4 \cdot \sqrt{S \cdot (S-AB) \cdot (S-AC) \cdot (S-BC)}}$$

wherein factor $S = \frac{AB + AC + BC}{2}$

Referring to FIG. 8B, it follows that radius R is equal to a radius AO from center O to first distal plunger position A, a radius BO from center O to second distal plunger position B, and a radius CO from center O to third distal plunger position C. An angle AOB between radii AO and BO is then calculated --according to the following equation derived from the law of cosines:

$$AOB = \cos^{-1}\left(\frac{(AO)^2 + (BO)^2 - (AB)^2}{2 \cdot AO \cdot BO}\right) \cdot \frac{360}{2 \cdot \pi}$$

Referring to FIG. 8C, values for radial distances AT and BT are equal to radial distances $d_1$ and $d_2$, respectively. Thus, an angle ABT between radial distances AT and BT is calculated according to the following equation derived from the law of sines:

$$ABT = \sin^{-1}\left(\frac{d_1 \cdot \sin\left(\frac{120 \cdot 2 \cdot \pi}{360}\right)}{AB}\right) \cdot \frac{360}{2 \cdot \pi}$$

Next, an angle ABO between chordal distance AB and radius BO and an angle OBT between radius BO and radial distance BT are calculated according to the following equations:

$$ABO = \frac{180 - AOB}{2}$$

OBT=ABT-ABO

It will be seen from FIG. 8C that a triangle is defined by three vertices corresponding to center O, centerline T, and second distal plunger position B. Because the values for two sides of this triangle, radius BO and radial distance BT, and the angle OBT therebetween are known, control/display console 60 can now calculate the value for the remaining side, which is the offset distance OT of centerline T from center O. Offset distance OT is calculated according to the following equation derived from the law of cosines:

$$OT = \sqrt{(BO)^2 + (d_2)^2 - \left(2 \cdot BO \cdot d_2 \cdot \cos\left(\frac{OBT \cdot 2 \cdot \pi}{360}\right)\right)}$$

The offset distance OT provides an accurate indication of the amount by which the centerline of shaft S is offset from the central axis of vessel V in any radial direction. This is because the calculation is based on three displacement magnitudes measured at three different positions of lateral plunger 44 within vessel V, and the relationships between the various points and distances observed within vessel V and described hereinabove can be resolved by trigonometric equations.

A preferred modification to the method described above yields the same result, i.e., calculation of offset distance OT, yet avoids the additional task of deriving values for radial distances AT, BT and CT from the first, second and third displacement magnitudes. In this preferred modification, .advantage is taken of the fact that the first, second and third displacement magnitudes measured by transducer 46 are linearly proportional to radial distances AT, BT and CT, respectively. Thus, radial distance $d_1$ is set equal to zero, radial distance $d_2$ is set equal to a value based on the second displacement magnitude relative to the first displacement magnitude, and radial distance $d_3$ is set equal to a value based on the third displacement magnitude relative to the first displacement magnitude. For example, $d_1=0$, $d_2=-0.1$, and $d_3=-0.9$. If such values for $d_1$, $d_2$ and $d_3$ are used and the above equations applied, the same value for offset distance OT is obtained.

Figure 9:
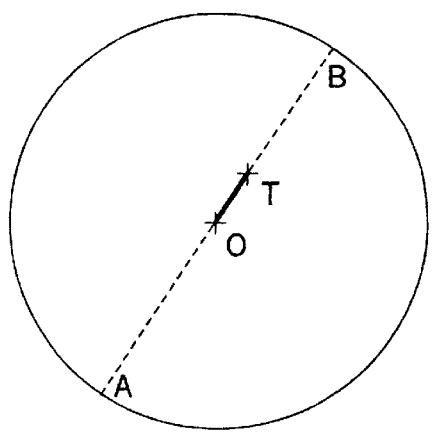
FIG. 9 is a geometric view illustrating another method for calculating the offset amount of the centerline of a shaft according to the present invention.

A further alternative method for calculating the amount by which the centerline of shaft S is offset from the central axis of vessel V will now be described with reference to FIG. 9. Lateral inside surface ID of vessel V is represented by a circle AB in FIG. 9, and has a center O through which the central axis of vessel V runs. The centerline of shaft S is represented by point T. If a diameter for circle AB is drawn through center O and centerline T, it is observed that a maximum displacement magnitude will be measured when lateral plunger 44 is disposed within vessel V along a maximum radial distance AT, and a minimum displacement magnitude will be measured when lateral plunger 44 is rotated 180° and disposed along a minimum radial distance BT. If lateral inside surface ID of vessel V were a perfect circle, an offset distance OT could be found by subtracting radius AO from radial distance AT or by subtracting radial distance BT from radius BO. A preferred method of calculation, however, is derived as follows.

It is observed that maximum radial distance AT=AO +OT and minimum radial distance BT=BO−OT. For purposes of calculation, lateral inside surface ID of vessel V is assumed to be a perfect circle such that AO=BO. Thus, minimum radial distance BT=AO−OT. Offset distance OT can be found by subtracting maximum radial distance AT from minimum radial distance BT as follows:

AT−BT=(AO+OT)−(AO−OT)=2OT

Therefore, $$OT = \frac{(AO+OT) - (AO-OT)}{2} = \frac{AT - BT}{2}$$

In order to implement this method, lateral plunger 44 is rotated 360°, i.e., one full revolution around the inside of vessel V. At predetermined intervals while lateral plunger 44 is rotating, e.g., every 5 ms, transducer 46 encodes the position of lateral plunger 44 to generate a data set consisting of a plurality of displacement magnitudes. From this data set, a maximum measured displacement magnitude $d_{MAX}$ and a minimum measured displacement magnitude $d_{MIN}$ are selected. An example of a subroutine that could perform this selection process can be constructed from the following steps:

1) READ a first displacement magnitude and STORE;
2) READ a second displacement magnitude and STORE;
3) IF second displacement magnitude<first displacement magnitude, THEN SET second displacement magnitude=$d_{MIN}$ AND SET first displacement magnitude=$d_{MAX}$, ELSE SET second displacement magnitude=$d_{MAX}$ AND SET first displacement magnitude=$d_{MIN}$;
4) READ a third displacement magnitude;
5) IF third displacement magnitude<$d_{MIN}$ THEN SET third displacement magnitude=$d_{MIN}$;
6) IF third displacement magnitude>$d_{MAX}$ THEN SET third displacement magnitude=$d_{MAX}$.

This procedure is repeated successively until each sampled displacement magnitude is determined to be either the maximum or minimum for the data set. Offset distance OT is then calculated according to the following equation:

$$OT = \frac{d_{MAX} - d_{MIN}}{2}$$

Referring primarily to FIGS. 7A and 7B, the operation of height measurement device 50 will now be described. Height measurement device 50 is affixed to shaft S. Prior to installation of shaft S in vessel V, a spherical object such as a stainless steel ball 65 having a predetermined uniform diameter is placed into vessel V. Stainless steel ball 65 will come to rest at a lowermost point 19 on the inside surface of hemispherical end region 16 of vessel V, thereby locating the true bottom of vessel V. Vertical plunger 54 is biased to a fully downwardly extended position. In order to obtain a zero reference position, end portion 54B of vertical plunger 54 is urged upwardly until good contact is made with the underside of paddle P or other operative component of shaft S. Shaft S is then inserted into vessel V at a normal operating position for shaft S.

Once shaft S has been installed, vertical plunger 54 moves downwardly until coming into contact with stainless steel ball 65. At this point, vertical plunger 54 will have displaced vertically with respect to the zero reference position. The distance by which vertical plunger 54 displaces is characterized as its displacement magnitude. Transducer 56 encodes the displaced position by reading the code strip mounted to vertical plunger 54 and generates a signal representative of the measured displacement magnitude, in a manner analogous to the interaction of transducer 46 and the code strip of lateral plunger 44 of centerline offset measurement device 40 described hereinabove. Transducer 56 sends the encoded signal to control/display console 60 (see FIG. 3A). The height of paddle P above lowermost point 19 of hemispherical end region 16 is most easily derived from the measured displacement magnitude by adding together the values for the displacement magnitude, the height of end portion 54B and the diameter of stainless steel ball 65.

As an alternative embodiment of the present invention, shaft centerline offset and height measurement system 30 can be modified to incorporate both the shaft centerline offset and height measurement functions in a single measurement device. That is, housing 42 or 52 can be adapted to accommodate both transducers 46 and 56, plungers 44 and 54, and their associated components described hereinabove. However, a preferred approach to this functional combination is to provide a more modular device which does not require the mounting of a single (and bulkier and heavier) housing to shaft S.

This preferred alternative embodiment will now be described with reference to FIGS. 10A, 10B, 11A, 11B and 12, illustrating a combined shaft centerline offset and height measurement device generally designated 70.

Instead of employing a housing to serve as a mounting assembly for centralizing the operative components of the present embodiment, a modified vessel centering ring 75 is provided. Modified vessel centering ring 75 includes a central region 75A having a bore 75B through which shaft S with paddle P or the like can be inserted.

Combined shaft centerline offset and height measurement device 70 includes a centerline offset measurement module generally designated 80 and a height measurement module generally designated 90. It will be noted that all operative components of combined shaft centerline and offset measuring device 70, including centerline offset measurement module 80 and a height measurement module 90, are mounted directly or indirectly to modified vessel centering ring 75, and thus operate independently of shaft S. Thus, while only one centerline offset measurement module 80 could be provided and rotated by means such as a turntable mounted to modified vessel centering ring 75, it is more advantageous to provide three centerline offset measurement modules 80, all of which are suspended from modified vessel centering ring 75 independently of shaft S. Moreover, as shown in FIGS. 10A and 10B, centerline offset measurement modules 80 are oriented 120O from each other, thereby eliminating the alignment and rotation steps attending centerline offset measurement device 40 in FIGS. 4A through 4D.

Figure 11A:
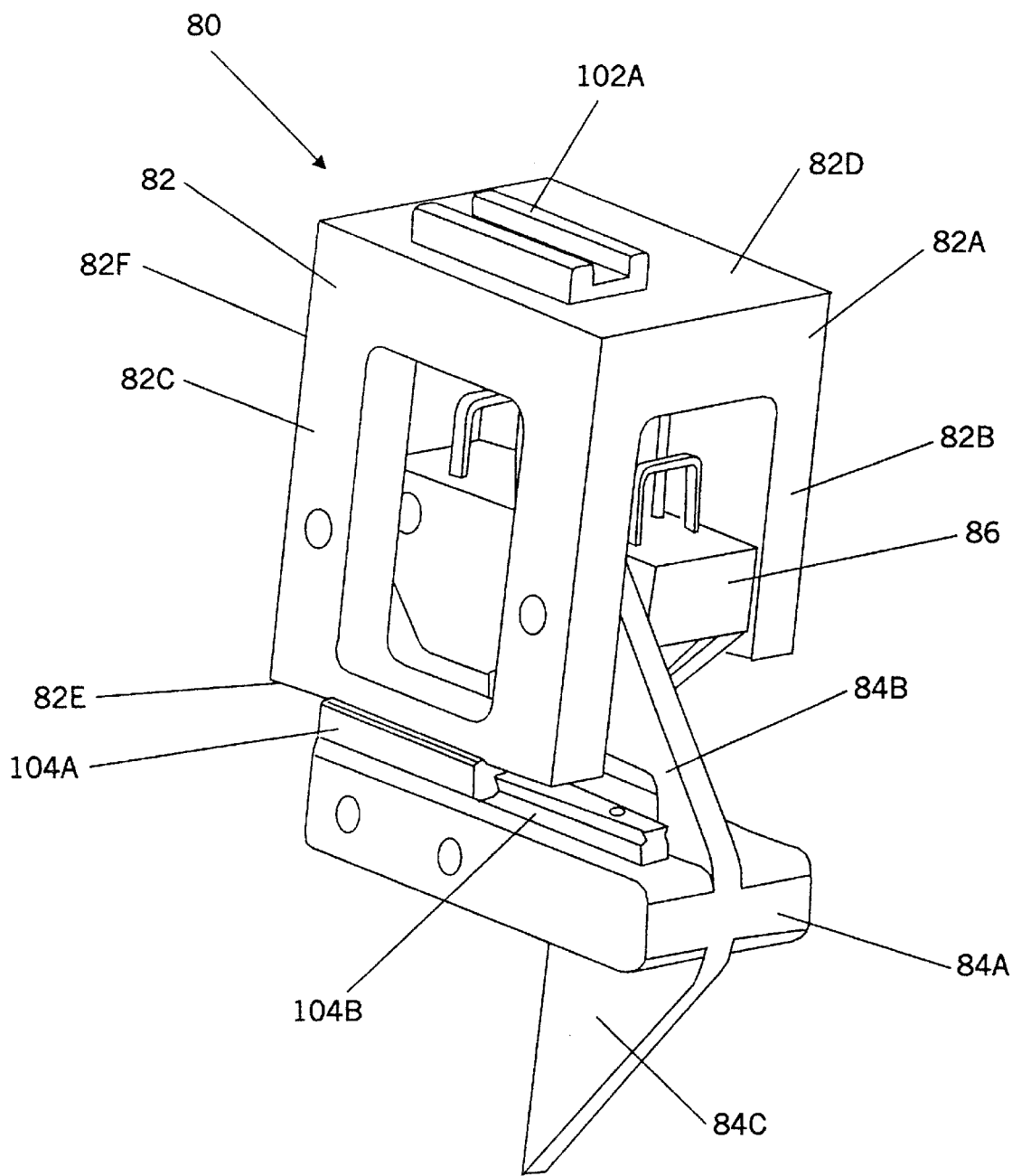
FIGS. 11A and 11B are detailed perspective views of a shaft centerline offset measurement module of the device in FIGS. 10A and 10B.
Figure 11B:
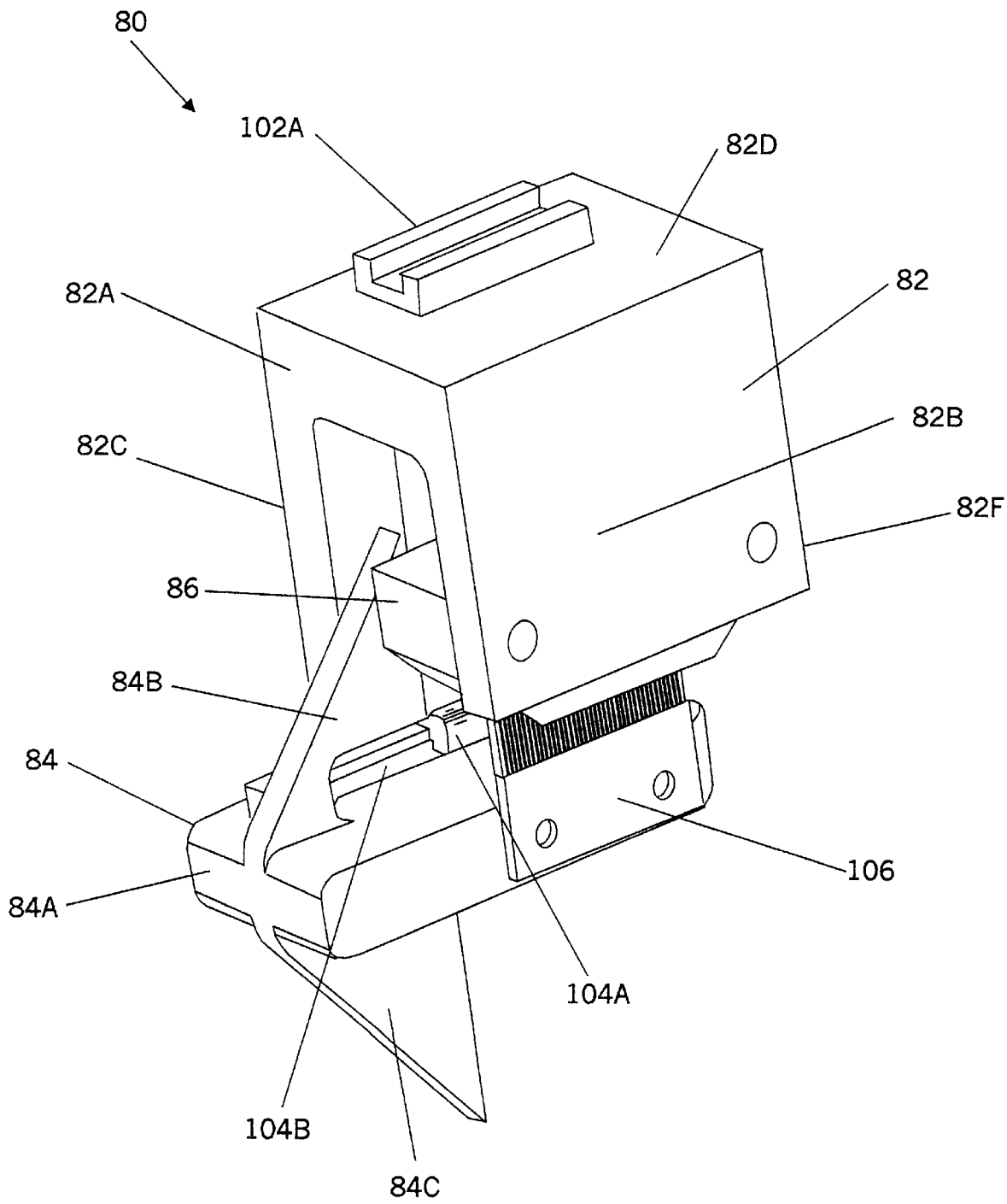

Referring to FIGS. 11A and 11B, each centerline offset measuring module 80 includes a sensor body 82 which serves as a mounting bracket for a lateral plunger 84 and a transducer 86. Sensor body 82 preferably has a U-shaped profile defined by a central region 82A and legs 82B and 82C. Transducer 86 is preferably secured directly to the inside of leg 82B of sensor body 82, and preferably is an optical linear encoder similar to transducers 46 and 56. An upper linear bearing 102A is attached to a top surface 82D of central region 82A and a lower linear bearing 104A is attached to an end 82E of leg 82C. A lower bearing track 104B is attached to each lateral plunger 84 and engages lower linear bearing 104A, thereby enabling lateral plunger 84 to slide laterally with respect to sensor body 82. A code strip 106 is fixedly secured to lateral plunger 84 to cooperate with transducer 86 in the manner described hereinabove.

Figure 10B:
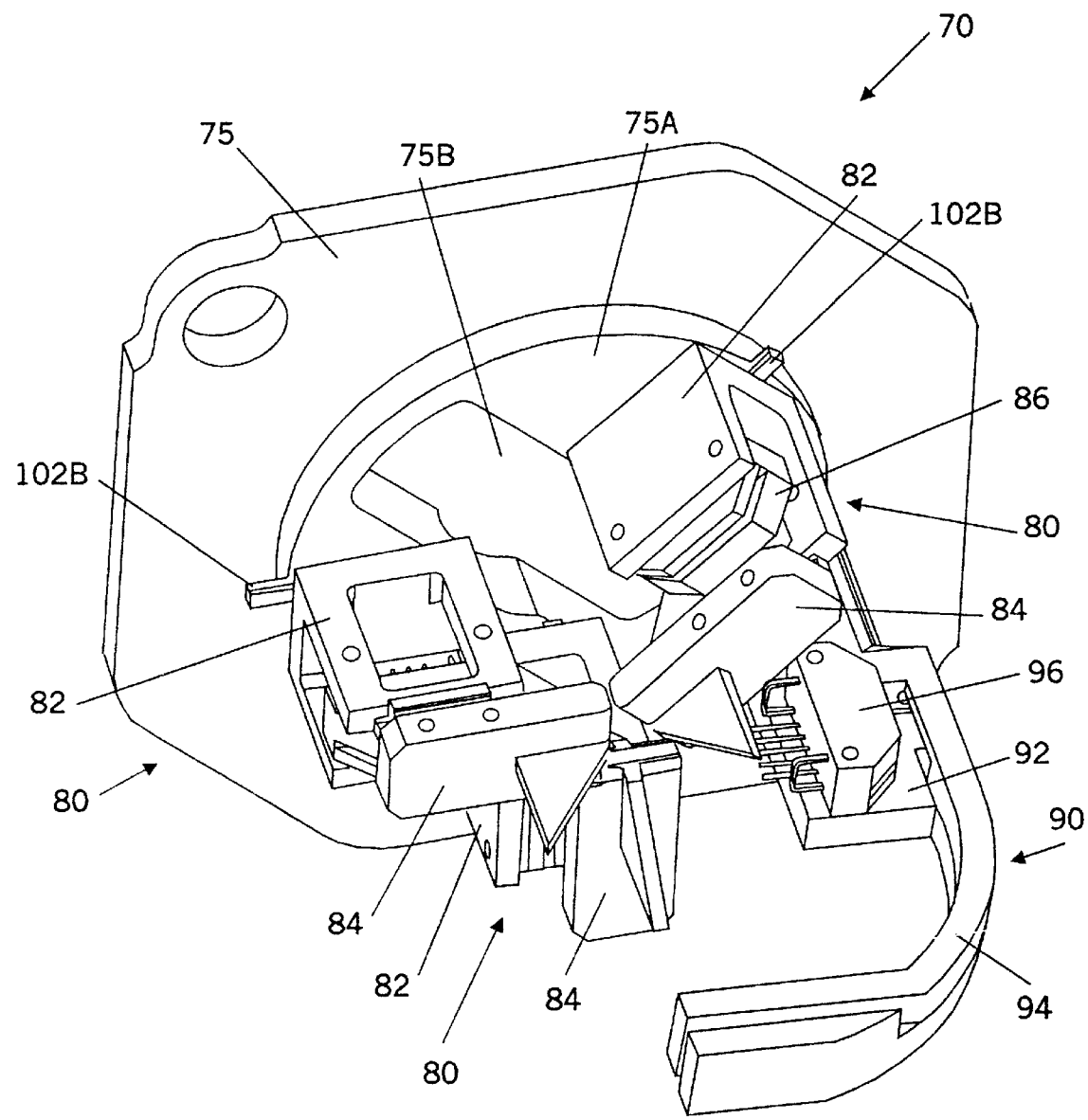

As shown in FIG. 10B, three upper bearing tracks 102B (of which only two are shown) are attached to central region 75A of modified vessel centering ring 75. Upper linear bearing 102A of each sensor body 82 engages a corresponding upper bearing track 102B to enable each sensor body 82 to slide laterally with respect to modified vessel centering ring 75. In the exemplary embodiment shown in FIGS. 10A and 10B, means such as springs (not shown) are provided respectively for biasing each lateral plunger 84 radially inwardly and for biasing each sensor body 82 radially outwardly. Thus, when shaft S is installed into vessel V, plunger tips 84A of lateral plungers 84 are biased to contact shaft S while rear faces 82F of sensor bodies 82 are biased to contact lateral inside surface ID of vessel V. Each lateral plunger 84 has upper and lower guide members 84B and 84C, respectively, to assist in urging lateral plungers 84 outwardly when shaft S is being inserted and removed from vessel V.

Figure 12:
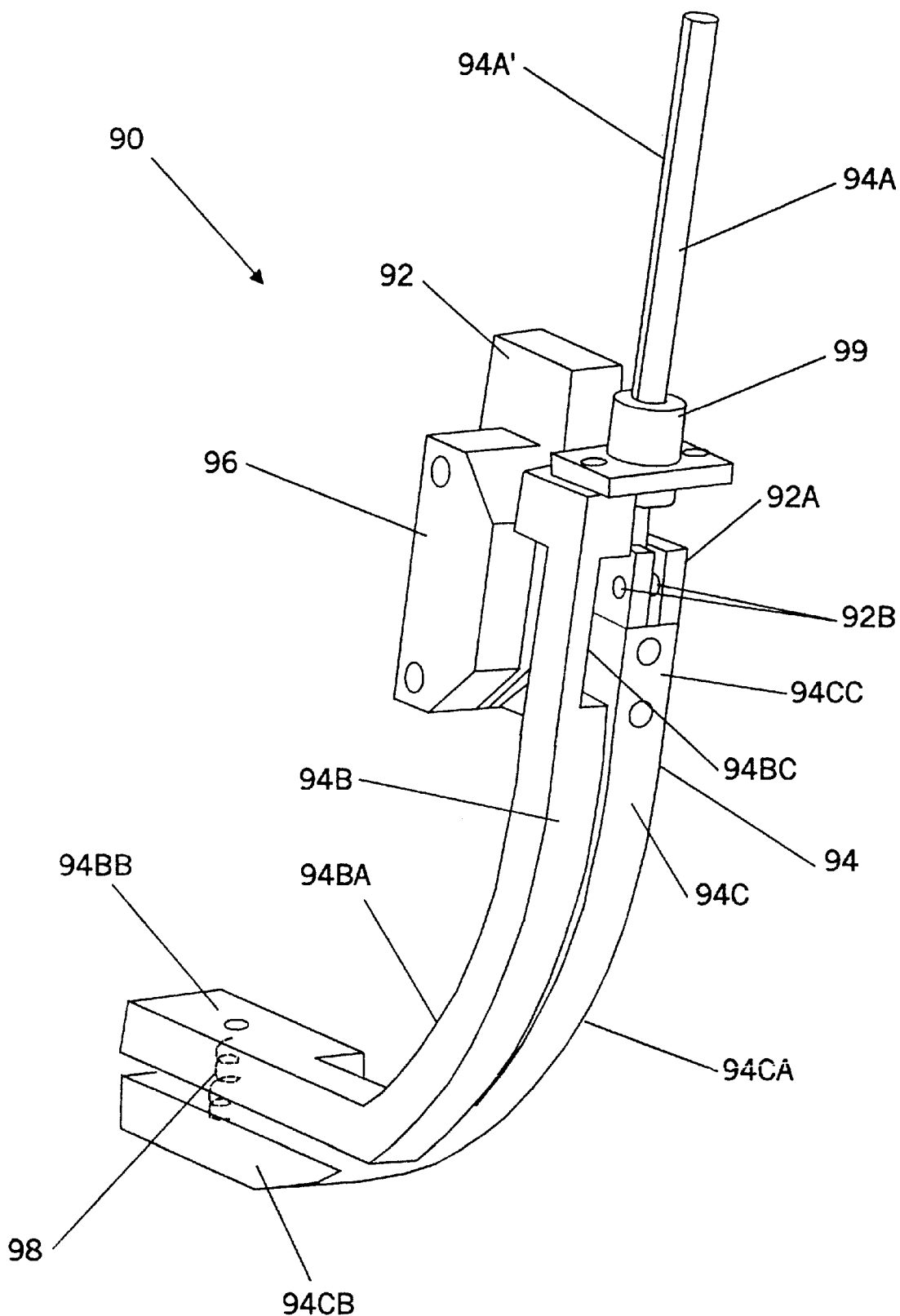
FIG. 12 is a detailed perspective view of a shaft height measurement module of the device in FIGS. 10A and 10B.

FIG. 12 is a detailed view of height measurement module 90, which is an alternative to incorporating the structure of height measurement device 50 described hereinabove. Height measurement module 90 includes a sensor mounting bracket 92, a vertical plunger 94, and a vertically-oriented transducer 96. Vertical plunger 94 preferably includes a vertical rail 94A, an upper arm 94B, and a lower arm 94C. Sensor mounting bracket 92 includes a clamping section 92A by which sensor mounting bracket 92 is fixedly secured to vertical rail 94A, such as by inserting vertical rail 94A through clamping section 92A and tightening clamping section 92A with a fastener (not shown) threaded into holes 92B.

In the preferred embodiment, lower arm 94C includes an arcuate section 94CA and a lower end portion 94CB extending horizontally from arcuate section 94CA. Likewise, upper arm 94B includes an arcuate section 94BA and a lower end portion 94BB extending horizontally from arcuate section 94BA. Arcuate sections 94BA and 94CA are disposed adjacent to each other, and upper end portion 94BB is disposed above lower end portion 94CB. Means such as a spring 98 is connected between upper end portion 94BB and lower end portion 94CB in order to vertically bias upper and lower end 94BB and 94CB portions away from each other.

Lower arm 94C is secured to sensor mounting bracket 92, or preferably is secured directly to vertical arm 94A such as by inserting vertical arm 94A into an upper portion of lower arm 94CC and employing fastening means similar to clamping section 92A. Upper arm 94B is mounted to an annular bearing 99 through which vertical rail 94A extends, thus enabling upper arm 94B to move vertically with respect to lower arm 94C and transducer 96. Vertical rail 94A is provided with a longitudinal groove 94A' which engages a complementary tongue (not shown) disposed within annular bearing 99, thereby preventing annular bearing 99 and upper arm 94B from rotating around vertical rail 94A. Upper arm 94B includes a recessed area 94BC into which a code strip (not shown) is attached to cooperate with transducer 96.

Vertical rail 94A is movably attached to modified vessel centering ring 75 in order to render combined shaft centerline offset and height measurement device 70 compatible with vessels V of different sizes. Preferably, an annular bearing (not shown) similar to annular bearing 99 is attached to modified vessel centering ring 75 and vertical rail 94A is extended therethrough. In addition, means such as a spring (not shown) is provided to bias vertical rail 94A (and thus height measurement module 90 in its entirety) downwardly.

To complete the measurement system, it will be readily apparent that combined shaft centerline and offset measurement device 70 is operable in conjunction with control/display console 60 in FIG. 3A, although some reprogramming is necessary. Combined shaft centerline and offset measurement device 70 can be made to communicate with control/display console 60 by running appropriate data lines such as conduits EC from transducers 86,96 to control/display console 60.

The operation of combined shaft centerline and offset measurement device 70 will now be described. Stainless steel ball 65 is inserted into vessel V in order to locate lowermost point 19 of hemispherical end region 16. Modified vessel centering ring 75, equipped with combined shaft centerline and offset measurement device 70, is then fitted onto rack 18 of dissolution testing station DTS over one of vessels V. At this time, rear face 82F of radially outwardly biased sensor body 82 of each centerline offset measurement module 80 makes contact with lateral inside surface ID of vessel V. Additionally, lower end portion 94CB of downwardly biased vertical plunger 94 of height measurement module 90 makes contact with stainless steel ball 65.

Shaft S is then lowered into vessel V to its normal operating position. Shaft S passes through bore 75B of modified vessel centering ring 75 while being lowered into vessel V. Also, paddle P contacts one or more upper guide members 84B of lateral plungers 84 while shaft S is being lowered into vessel V, thus urging one or more of lateral plungers 84 outwardly to clear the way for paddle P to pass downwardly. Once shaft S reaches its normal operating position, plunger tips 84A of radially inwardly biased lateral plungers 84 are in full contact with shaft S.

Assuming shaft S is offset from the central axis of vessel V, one or more of lateral plungers 84 of centerline offset measurement modules 80 will have displaced outwardly with respect to a predetermined zero reference position for displaced lateral plunger or plungers 84. Hence, lateral plungers 84 operate in a manner analogous to lateral plunger 44 of centerline offset measurement device 40. Each lateral plunger 84 if displaced will have moved by a distance equal to a displacement magnitude along the radial direction of that particular lateral plunger 84. This physical event is measured and converted into an electrical signal by the coaction of transducer 86 and its associated code strip 106 as described hereinabove. Accordingly, three signals representing the displacement magnitudes at the 120° positions along lateral inside surface ID of vessel V are sent to control/display console 60. Offset distance OT is then preferably calculated by employing the sequence of steps including the trigonometric equations described hereinabove.

Height measurement module 90 also operates when shaft S is installed in vessel V. Before the bottom end of shaft S or its paddle P reaches its lowermost position within vessel V, upper end portion 94BB of upper arm 94B of vertical plunger 94 is biased in its highest position above lower end portion 94CB of lower arm 94C. This constitutes a zero reference position for vertical plunger 94. As shaft S is being lowered into vessel V, paddle P makes contact with upper end portion 94BB. By the time shaft S reaches its final, normal operating position, paddle P will have urged upper end portion 94BB downwardly towards lower end portion 94CB against the biasing force of spring 98. As the code strip for vertical plunger 94 is fixedly mounted in recessed area 94BC of upper arm 94B, the code strip moves downwardly by the same distance as upper end portion 94BB. This distance constitutes the displacement magnitude for vertical plunger 94, which is encoded by transducer 96, and a signal is sent to control/display console 60 for further processing. One way to derive or interpret the height of paddle P above lowermost point 19 of vessel V is to add together values for the measured displacement magnitude, the height of upper end portion 94BB, the height of lower end portion 94CB, and the diameter of stainless steel ball 65.

It will be understood that while the Figures depict control/display console 60 as being portable and designed for remote operation, the present invention encompasses a variation wherein control/display console 60 is integrated into dissolution testing station DTS. For example, the operative components of control/display console 60 can be housed within programmable systems control module 20 of dissolution testing station DTS (see FIG. 2).

Figures 13, 13A:
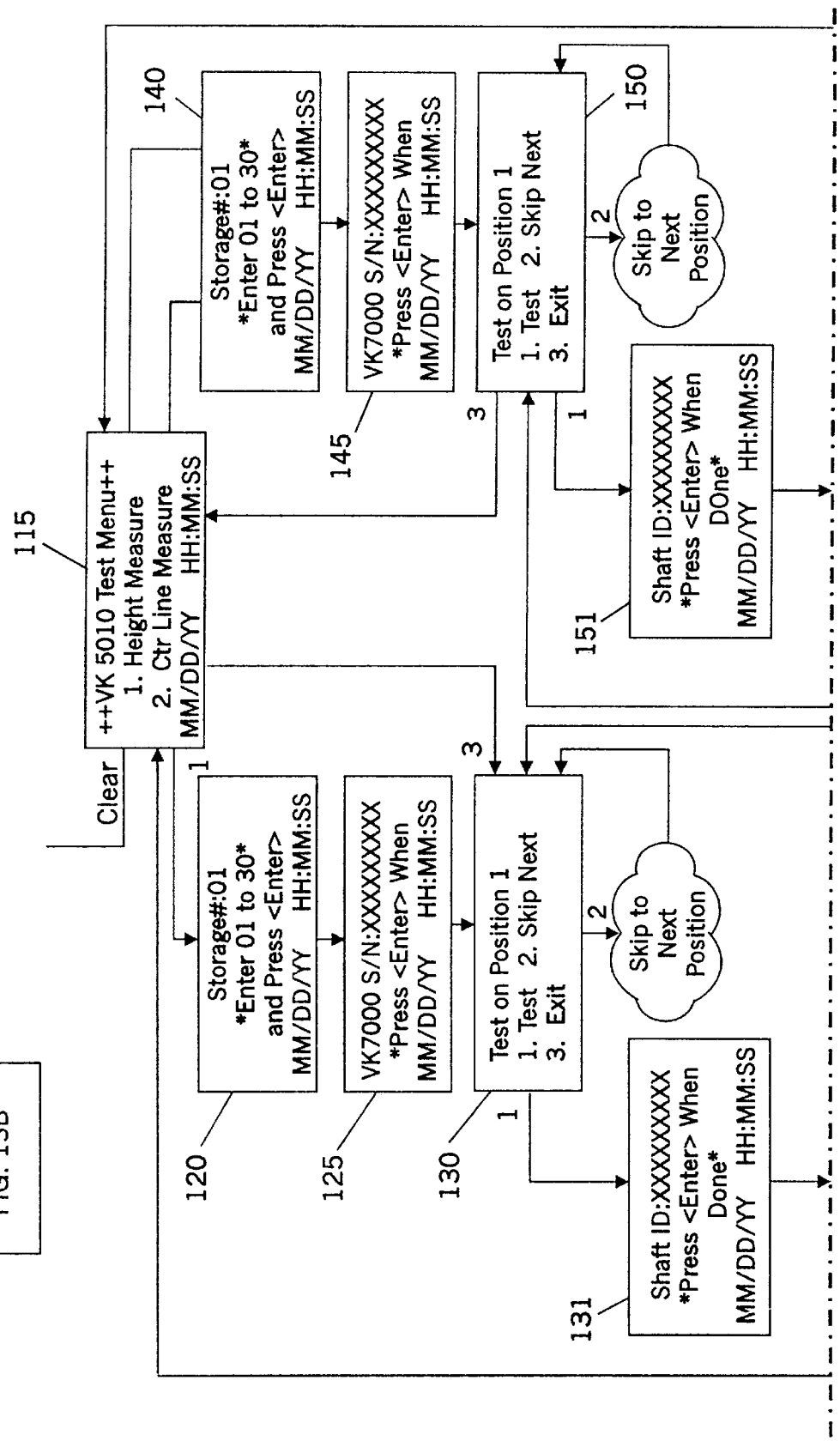
FIGS. 13A and 13B are a flow diagram of a test routine according to the present invention.
Figure 13B:
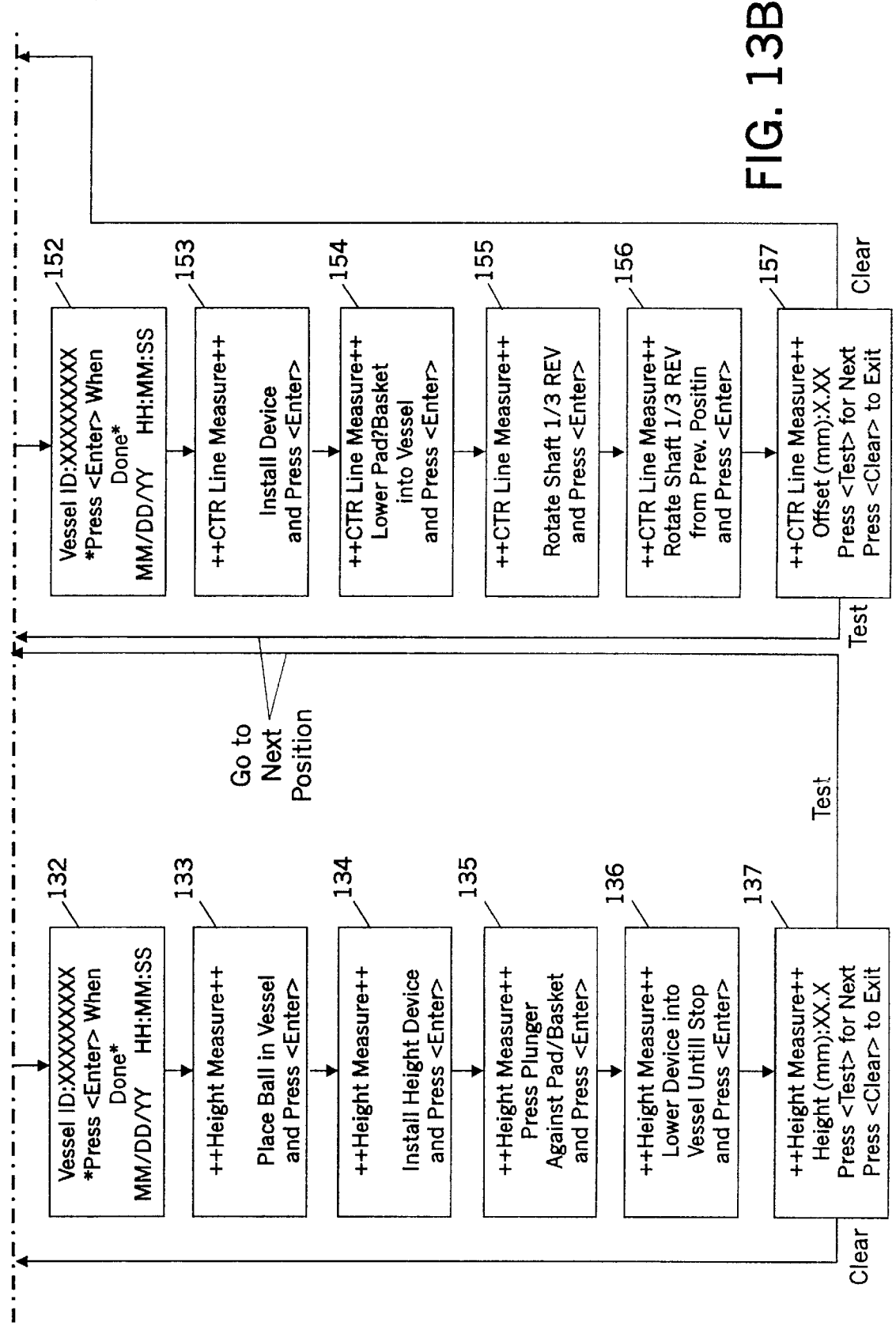

FIGS. 13A and 13B illustrate by way of example a flow diagram of a test routine executable by software written for control/display console 60. The particular test routine illustrated manages the operation of shaft centerline offset and height measurement system 30 with centerline offset measurement device 40 and height measurement device 50. It will be understood, however, that the software can be rewritten without undue experimentation and adapted for use of control/display console 60 with combined shaft centerline offset and height measurement device 70. It is also to be noted that this test routine can be configured, for example, to test up to 30 dissolution testing stations DTS and up to 8 shafts S and corresponding vessels V per dissolution testing station DTS. Therefore, a total of 240 shaft sites can be tested in a single test routine if desired.

Referring again to FIGS. 13A and 13B, display screen 60C of control/display console 60 displays a main menu at step 115, prompting the user to select either a test run for shaft height measurement or a test run for shaft offset measurement. If the user selects a test run for shaft height measurement, a shaft height measurement subroutine 120–137 is initiated. On the other hand, if the user selects a test run for shaft offset (or "ctr line") measurement, a shaft offset measurement subroutine 140–157 is initiated.

When the shaft height measurement subroutine is initiated, the user is prompted at step 120 to assign an integer from 1 to 30 to the dissolution testing station presently being tested in order to distinguish that testing station from other testing stations to be tested. The user is then prompted at step 125 to input an identification for that particular testing station, such as a serial number. Shafts operating in that testing station are assigned numbers according to the respective positions of the shafts in the testing station, such as 1 through 6 or 1 through 8. Thus, the user is prompted at step 130 to either initiate testing of a particular shaft, proceed to the next shaft, or exit the shaft height measurement subroutine and return to the main menu.

If the user desires to test that particular shaft, the user is prompted at step 131 to input an identification for the shaft, such as a serial number. Next, the user is prompted at step 132 to input an identification for the vessel in which the shaft operates. The user is then prompted to place the stainless steel ball into the vessel at step 133, install the shaft height measurement device at step 134, press the vertical plunger upwardly against the paddle or basket of the shaft in order to obtain a zero reference reading at step 135, and lower the shaft equipped with the height measurement device into the vessel at step 136. Once the shaft height measurement has been taken and appropriately interpreted, a readout or indication of the shaft height is displayed at step 137 and the user is prompted to test another shaft in the particular testing station being tested.

When the shaft centerline offset measurement subroutine is initiated by selection at step 115, the user is prompted at step 140 to assign an integer to the dissolution testing station presently being tested. The user is then prompted at step 145 to input an identification for that particular testing station. Next, the user is prompted at step 150 to either initiate testing of a particular shaft identified by its position number, proceed to the next shaft, or exit the shaft centerline offset measurement subroutine and return to the main menu.

If the user desires to test that particular shaft, the user is prompted at step 151 to input an identification for the shaft. Next, the user is prompted at step 152 to input an identification for the vessel in which the shaft operates. The user is then prompted to install the shaft centerline offset measurement device at step 153, and to lower the shaft equipped with the offset measurement device into the vessel at step 154. After a key input is entered at this position, the user is prompted at step 155 to rotate the shaft 120°. A key input is requested to indicate the completion of this step. The user is then prompted at step 156 to rotate the shaft another 120°, and a key input is requested to indicate the completion of this step. Once the measurements taken at these positions have been appropriately interpreted and the offset distance calculated, a readout or indication of the shaft centerline offset is displayed at step 157 and the user is prompted to test another shaft in the particular testing station being tested.

These steps are repeated for every shaft and dissolution testing station desired by the user to be tested.

It will be understood that in the case where the centerline offset is measured by making one full rotation around the vessel in order to sample a plurality of displacements, the steps of the test routine are modified accordingly. It will also be understood that in the case where a testing routine such as that just described is adapted for use in conjunction with combined shaft centerline offset and height measurement device 70, the total number of steps required by the test routine can be reduced.

It will be further understood that various details of the invention may be changed without departing from the scope of the invention. Furthermore, the foregoing description is for the purpose of illustration only, and not for the purpose of limitation—the invention being defined by the claims.

What is claimed is:

1. An apparatus mountable to a shaft disposed within a vessel and adapted for measuring the magnitude by which the centerline of the shaft is offset from the central axis of the vessel, comprising:
   (a) a housing comprising a coupling component for coupling the housing to the shaft;
   (b) a plunger slidably mounted to the housing, the plunger having an outer section extending radially outwardly beyond a wall of the housing, and having means for biasing the plunger radially outwardly;
   (c) a transducer operatively mounted to the housing and adapted to encode positions of the plunger and to produce an electrical signal proportional to a change in position resulting from displacement of the plunger; and
   (d) means for transferring the signal away from the housing.

2. The apparatus according to claim 1 wherein the coupling component includes a longitudinal recess defined by a recess wall extending inwardly toward an interior of the housing from a rear face of the housing.

3. The apparatus according to claim 2 wherein the recess wall has a cylindrical profile.

4. The apparatus according to claim 2 wherein the longitudinal recess includes an upper section extending downwardly from a top face of the housing, the upper section having a width greater than a width of an adjacent section of the longitudinal recess, the apparatus further comprising means disposed in the upper section for removably securing the housing to the shaft.

5. The apparatus according to claim 4 wherein the removably securing means includes a clip extending outwardly from the recess wall within the upper section, the clip including a pair of resilient prongs.

6. The apparatus according to claim 5 wherein each prong has an inside surface, and the clip and inside surfaces of the prongs cooperatively define a cylindrical profile.

7. The apparatus according to claim 1 wherein the housing has a bottom face and a groove extending inwardly toward an interior of the housing from the bottom face.

8. The apparatus according to claim 1 wherein the plunger is slidably disposed within the housing and the outer section of the plunger extends radially outwardly through a hole in the wall of the housing.

9. The apparatus according to claim 1 further comprising a plate mounted to the plunger and including a plurality of equally spaced lines readable by the transducer, wherein the transducer is an optical encoder disposed within the housing and the number of lines read by the transducer corresponds to a magnitude of the change in position of the plunger.

10. The apparatus according to claim 1 wherein the signal transferring means includes an electrical conduit.

11. The apparatus according to claim 1 comprising a device for interpreting the signal, the device disposed remotely in relation to the housing and communicating with the signal transferring means.

12. The apparatus according to claim 11 wherein the signal interpreting device comprises a display component for displaying the interpreted signal in human-readable form.

13. An apparatus mountable to a shaft disposed within a vessel and adapted for measuring the magnitude by which the centerline of the shaft is offset from the central axis of the vessel, comprising:

(a) a housing comprising a rear face, a top face, a longitudinal recess, and a clip, the longitudinal recess defined by a recess wall extending inwardly toward an interior of the housing, the longitudinal recess comprising an upper section extending downwardly from the top face, the upper section having a width greater than a width of an adjacent section of the longitudinal recess, the clip extending outwardly from the recess wall within the upper section and comprising a pair of resilient prongs;

(b) a plunger slidably mounted to the housing, the plunger having an outer section biased to extend radially outwardly beyond a wall of the housing;

(c) a transducer operatively mounted to the housing and adapted to encode positions of the plunger and to produce an electrical signal proportional to a change in position resulting from displacement of the plunger; and (d) means for transferring the signal away from the housing.

14. The apparatus according to claim 13 wherein each prong has an inside surface, and the clip and inside surfaces of the prongs cooperatively define a cylindrical profile.

15. The apparatus according to claim 13 wherein the housing has a bottom face and a groove extending inwardly toward an interior of the housing from the bottom face.

16. The apparatus according to claim 13 wherein the plunger is slidably disposed within the housing and the outer section of the plunger extends radially outwardly through a hole in the wall of the housing.

17. The apparatus according to claim 13 further comprising a plate mounted to the plunger and including a plurality of equally spaced lines readable by the transducer, wherein the transducer is an optical encoder disposed within the housing and the number of lines read by the transducer corresponds to a magnitude of the change in position of the plunger.

18. The apparatus according to claim 13 wherein the signal transferring means includes an electrical conduit.

19. The apparatus according to claim 13 comprising a device for interpreting the signal, the device disposed remotely in relation to the housing and communicating with the signal transferring means.

20. The apparatus according to claim 19 wherein the signal interpreting device comprises a display component for displaying the interpreted signal in human-readable form.

21. An apparatus mountable to a shaft disposed within a vessel and adapted for measuring the magnitude by which the centerline of the shaft is offset from the central axis of the vessel, comprising:

(a) a housing;

(b) a plunger slidably mounted to the housing, the plunger having an outer section biased to extend radially outwardly beyond a wall of the housing;

(c) a transducer operatively mounted to the housing and adapted to encode positions of the plunger and to produce an electrical signal proportional to a change in position resulting from displacement of the plunger;

(d) means for transferring the signal away from the housing; and (e) a device for interpreting the signal, the device disposed remotely in relation to the housing and communicating with the signal transferring means.

22. The apparatus according to claim 21 wherein the housing includes a rear face and a longitudinal recess defined by a recess wall extending inwardly toward an interior of the housing from the rear face.

23. The apparatus according to claim 22 wherein the recess wall has a cylindrical profile.

24. The apparatus according to claim 22 wherein the longitudinal recess includes an upper section extending downwardly from a top face of the housing, the upper section having a width greater than a width of an adjacent section of the longitudinal recess, the apparatus further comprising means disposed in the upper section for removably securing the housing to the shaft.

25. The apparatus according to claim 24 wherein the removably securing means includes a clip extending outwardly from the recess wall within the upper section, the clip including a pair of resilient prongs.

26. The apparatus according to claim 25 wherein each prong has an inside surface, and the clip and inside surfaces of the prongs cooperatively define a cylindrical profile.

27. The apparatus according to claim 21 wherein the housing has a bottom face and a groove extending inwardly toward an interior of the housing from the bottom face.

28. The apparatus according to claim 21 wherein the plunger is slidably disposed within the housing and the outer section of the plunger extends radially outwardly through a hole in the wall of the housing.

29. The apparatus according to claim 21 further comprising a plate mounted to the plunger and including a plurality of equally spaced lines readable by the transducer, wherein the transducer is an optical encoder disposed within the housing and the number of lines read by the transducer corresponds to a magnitude of the change in position of the plunger.

30. The apparatus according to claim 21 wherein the signal transferring means includes an electrical conduit.

31. The apparatus according to claim 30 wherein the signal interpreting device comprises a display component for displaying the interpreted signal in human-readable form.

* * * * *